(12) United States Patent
Altschuler et al.

(10) Patent No.: US 10,815,477 B2
(45) Date of Patent: *Oct. 27, 2020

(54) METHODS AND SYSTEMS FOR IDENTIFYING PATIENT SPECIFIC DRIVER MUTATIONS

(71) Applicant: NOVELLUSDX LTD., Jerusalem (IL)

(72) Inventors: Yoram Altschuler, Mevasseret Zion (IL); Gabi Tarcic, Mevasseret Zion (IL)

(73) Assignee: NOVELLUSDX LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/032,425

(22) Filed: Jul. 11, 2018

(65) Prior Publication Data

US 2018/0320167 A1  Nov. 8, 2018

Related U.S. Application Data

(63) Continuation of application No. 14/761,002, filed as application No. PCT/IL2014/050054 on Jan. 16, 2014, now Pat. No. 10,047,356.

(60) Provisional application No. 61/753,458, filed on Jan. 17, 2013.

(51) Int. Cl.
| | |
|---|---|
| *C12Q 1/68* | (2018.01) |
| *C12N 15/10* | (2006.01) |
| *G01N 21/64* | (2006.01) |
| *C12Q 1/6886* | (2018.01) |

(52) U.S. Cl.
CPC ....... *C12N 15/1055* (2013.01); *C12Q 1/6886* (2013.01); *G01N 21/6428* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs |
| 3,839,153 A | 10/1974 | Schuurs |
| 3,850,578 A | 11/1974 | McConnell |
| 3,850,752 A | 11/1974 | Schuurs |
| 3,853,987 A | 12/1974 | Dreyer |
| 3,867,517 A | 2/1975 | Ling |
| 3,879,262 A | 4/1975 | Schuurs |
| 3,901,654 A | 8/1975 | Gross |
| 3,935,074 A | 1/1976 | Rubenstein |
| 3,984,533 A | 10/1976 | Uzgiris |
| 3,996,345 A | 12/1976 | Ullman |
| 4,034,074 A | 7/1977 | Miles |
| 4,098,876 A | 7/1978 | Piasio |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands |
| 5,011,771 A | 4/1991 | Bellet |
| 5,192,659 A | 3/1993 | Simons |
| 5,272,057 A | 12/1993 | Smulson |
| 5,281,521 A | 1/1994 | Trojanowski |
| 5,792,638 A | 8/1998 | Aaronson |
| 2003/0211462 A1 | 11/2003 | Shen |
| 2004/0115659 A1 | 6/2004 | Geiger |

FOREIGN PATENT DOCUMENTS

| | | |
|---|---|---|
| JP | 2000-509827 A | 8/2000 |
| WO | 2008/148072 A2 | 12/2008 |

OTHER PUBLICATIONS

Nagpal et al., (2011) Natural loss-of-function mutation of myeloid differentiation protein 88 disrupts its ability to form Myddosomes. J Biol Chem 286(13): 11875-11882, 8 pages.
Togawa et al., (2009) Functional analysis of mutant human somatostatin receptor using a yeast-based fluorescence reporter assay. Journal of Bioscience and Bioengineering 108(Supplement 1): p. S108, EP-P28, 1 page.
Togawa et al., (2010) Importance of asparagine residues at positions 13 and 26 on the amino-terminal domain of human somatostatin receptor subtype-5 in signalling. J Biochem 147(6): 867-873; 7 pages.
Office Action dated Aug. 13, 2019 issued in corresponding Japanese Patent Application No. 2018-180860 with English translation, 9 pages.
Bashashati, et al., (2012) DriverNet: uncovering the impact of somatic driver mutations on transcriptional networks in cancer. Genome biology 13(12): R124; pp. 1-14.
Brownawell, et al., (2001) Inhibition of nuclear import by protein kinase B (Akt) regulates the subcellular distribution and activity of the forkhead transcription factor AFX. Mol Cell Biol 21(10): 3534-3546.
Cagnol, and Rivard, (2013) Oncogenic KRAS and BRAF activation of the MEK/ERK signaling pathway promotes expression of dual-specificity phosphatase 4 (DUSP4/MKP2) resulting in nuclear ERK1/2 inhibition. Oncogene 32(5): 564-576.
Hao, et al., (2005) Screening of differential expression genes between primary breast cancer and its lymph node metastasis using single primer amplification of cDNA for microarray. Natl Med J china 85(6): 385-390.
Kau, et al., (2003) A chemical genetic screen identifies inhibitors of regulated nuclear export of a Forkhead transcription factor in PTEN-deficient tumor cells. Cancer Cell 4(6): 463-476.
Kau, et al., (2004) Nuclear transport and cancer: from mechanism to intervention. Nat Rev Cancer 4(2): 106-117.
Knauer, et al., (2005) Translocation biosensors to study signal-specific nucleo-cytoplasmic transport, protease activity and protein-protein interactions. Traffic 6(7): 594-606.
Kurman, and Shih, (2011) Molecular pathogenesis and extraovarian origin of epithelial ovarian cancer—shifting the paradigm. Human pathology 42(7): 918-931.

(Continued)

*Primary Examiner* — Celine X Qian
(74) *Attorney, Agent, or Firm* — J.A. Lindeman & Co. PLLC

(57) ABSTRACT

Methods for identifying patient specific driver mutations are provided. The methods provided identify specific patient derived markers associated with aberrant signal transduction pathways, in biological samples of a cancer patient.

6 Claims, 23 Drawing Sheets
Specification includes a Sequence Listing.

(56) References Cited

OTHER PUBLICATIONS

Kyung, et al., (2013) Functional analysis of non-hotspot AKT1 mutants found in human breast cancers identifies novel driver mutations: implications for personalized medicine. Oncotarget 4(1): 29-34.

Morrison, et al., (2005) Apo2L/TRAIL induction and nuclear translocation of inositol hexakisphosphate kinase 2 during IFN-beta-induced apoptosis in ovarian carcinoma. Biochem J 385(Pt 2): 595-603.

Overdevest, et al., (2009) Utilizing the molecular gateway: the path to personalized cancer management. Clin Chem 55(4): 684-697.

Sawey, et al., (2011) Identification of a therapeutic strategy targeting amplified FGF19 in liver cancer by Oncogenomic screening. Cancer Cell 19(3): 347-358.

Smith, et al., (2009) Multiplexed fluorescence imaging of tumor biomarkers in gene expression and protein levels for personalized and predictive medicine. Curr Mol Med 9(8): 1017-1023.

Stricker, et al., (2011) Molecular profiling of cancer—the future of personalized cancer medicine: a primer on cancer biology and the tools necessary to bring molecular testing to the clinic. Semin Oncol 38(2): 173-185.

Van't Veer, and Bernards, (2008) Enabling personalized cancer medicine through analysis of gene-expression patterns. Nature 452(7187): 564-570.

Wood, et al., (2012) MicroSCALE screening reveals genetic modifiers of therapeutic response in melanoma. Sci Signal 5(224): rs4; 20 pages.

Xiao, et al., (2005) Antitumor effects of Cyclin D1 antisense cDNA on human hepatocellular carcinoma. Chin J Exp Surg 22(8): 927-930.

Yoshikawa, et al., (2004) Transfection microarray of human mesenchymal stem cells and on-chip siRNA gene knockdown. Journal of controlled release 96(2): 227-232.

Zanella, et al., (2007) An HTS approach to screen for antagonists of the nuclear export machinery using high content cell-based assays. Assay Drug Dev Technol 5(3): 333-341.

Zhang, et al., (2012) Differential expression of nuclear factor of activated T cell gene family member mRNA in hepatocellular carcinoma tissues and adjacent non-tumorous tissues. Chin J Exp Surg 29(2): 237-239.

Office Action dated Jan. 9, 2018 issued in corresponding Japanese Patent Application No. 2015-553227 with English translation, 16 pages.

Hyper subcellular translocation of ERK2 in response to expression of KRAS driver mutation Hyper subcellular translocation of
ERF in response to expression of
KRAS driver mutation Hyper subcellular translocation of JNK1A1 in response to expression of KRAS driver mutation Hyper subcellular translocation of AKT1 in response to expression of KRAS driver mutation Decreased subcellular translocation of RelA in response to expression of AKT2 unknown mutation Increased subcellular translocation
of AKT1 in response to expression
of AKT3 known mutation Increased subcellular translocation of RelA in response to expression of AKT3 known mutation Increased subcellular
translocation of mutant SMAD2

Increased subcellular translocation
of ERK2 in response to expression
of FGFR1 unknown mutation Increased subcellular translocation
of JNK1 in response to expression
of FGFR1 unknown mutation Decreased subcellular translocation
of P38 in response to expression of
FGFR1 unknown mutation No effect on subcellular translocation of STAT3 in response to expression of FGFR1 unknown mutation No effect on subcellular translocation of AKT1 in response to expression of FGFR1 unknown mutation Increased subcellular
translocation of ERK2 in response
to expression of BRaf known and
unknown driver mutation Increased subcellular translocation of ERF in response to expression of BRaf known and unknown driver mutation Increased subcellular translocation
of RelA in response to expression of
EGFR known mutations Mutation specific increased
subcellular translocation of AKT1
in response to expression of EGFR
known mutations Increased subcellular translocation
of JNK1 in response to expression
of specific EGFR known mutations Oncogenic map No effect on subcellular translocation of P38 in response to expression of EGFR known mutation Mutation specific increased subcellular translocation of AKT1 in response to expression of EGFR known mutations

SEQUENCE LISTING

```
<160> NUMBER OF SEQ ID NOS: 47

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
atgagcgacg tggctattgt                                             20

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
tcaggccgtg ccgctggc                                               18

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
atggcggcgc tgagcggtg                                              19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tcagtggaca ggaaacgcac                                             20

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
atgcgaccct ccgggacg                                               18

<210> SEQ ID NO 6
<211> LENGTH: 24
<212> TYPE: DNA
<213> ORGANISM: Artificial Sequence
```

```
<220> FEATURE:
<223> OTHER INFORMATION: Primer

<400> SEQUENCE: 6
tcatgctcca ataaattcac tgct                                      24

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
atgacggaat ataagctggt ggt                                       23

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tcaggagagc acacacttgc                                           20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
atgcccaaga agaagccgac                                           20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
ttagacgcca gcagcatgg                                            19

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
atgactgagt acaaactggt ggt                                       23

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ttacatcacc acacatggca                                           20
```

```
<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
atggggactt cccatccgg                                              19

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
ttacaggaag ctgtcttcca cc                                          22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
atgcctccac gaccatcatc                                             20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcagttcaat gcatgctgtt                                             20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
atgacagcca tcatcaaaga ga                                          22

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
tcagactttt gtaatttgtg tatgc                                       25

<210> SEQ ID NO 19
<211> LENGTH: 20
<212> TYPE: DNA
<213> ORGANISM: Artificial Sequence
<220> FEATURE:
<223> OTHER INFORMATION: Primer
```

```
<400> SEQUENCE: 19
atggagcaca tacagggagc                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ctagaagaca ggcagcctcg                                              20

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
atggaggagc cgcagtca                                                18

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tcagtctgag tcaggccctt                                              20

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
atgaatgagg tgtctgtcat caaag                                        25

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
tcactcgcgg atgctgg                                                 17

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
atgagcgatg ttaccattgt g                                            21
```

```
<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ttattctcgt ccacttgcag ag                                              22

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
atgtggagct ggaagtgc                                                   18

<210> SEQ ID NO 28
<211> LENGTH: 17
<212> TYPE: DNA
<213> ORGANISM: Artificial Sequence
<220> FEATURE:
<223> OTHER INFORMATION: Primer

<400> SEQUENCE: 28
tcagcggcgt ttgagtc                                                    17

<210> SEQ ID NO 29
<211> LENGTH: 17
<212> TYPE: DNA
<213> ORGANISM: Artificial Sequence
<220> FEATURE:
<223> OTHER INFORMATION: Primer

<400> SEQUENCE: 29
atggtcagct ggggtcg                                                    17

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
tcatgtttta acactgccgt ttatg                                           25

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
gcctgctgaa aatgactgaa tataaac                                         27

<210> SEQ ID NO 32
<211> LENGTH: 31
<212> TYPE: DNA
<213> ORGANISM: Artificial Sequence
<220> FEATURE:
<223> OTHER INFORMATION: Primer
```

```
<400> SEQUENCE: 32
ttacataatt acacactttg tctttgactt c                              31

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
atgtcgtcca tcttgccatt c                                        21

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
ttatgacatg cttgagcaac g                                        21

<210> SEQ ID NO 35
<211> LENGTH: 16
<212> TYPE: DNA
<213> ORGANISM: Artificial Sequence
<220> FEATURE:
<223> OTHER INFORMATION: Primer

<400> SEQUENCE: 35
atggcggcgg cggcgg                                              16

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
ttaagatctg tatcctgg                                            18

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
atgaagaccc cggcggacac                                          20

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
tcaggagtct cggtgctcc                                           19
```

```
<210> SEQ ID NO 39
<211> LENGTH: 17
<212> TYPE: DNA
<213> ORGANISM: Artificial Sequence
<220> FEATURE:
<223> OTHER INFORMATION: Primer

<400> SEQUENCE: 39
atgagcagaa gcaagcg                                                  17

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
tcactgctgc acctgtgc                                                 18

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
atggacgaac tgttccccct                                               20

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
taggagctga tctgactcag c                                             21

<210> SEQ ID NO 43
<211> LENGTH: 14
<212> TYPE: DNA
<213> ORGANISM: Artificial Sequence
<220> FEATURE:
<223> OTHER INFORMATION: Primer

<400> SEQUENCE: 43
atgtcgggcc ctcg                                                     14

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tcactgctca atctccaggc                                               20

<210> SEQ ID NO 45
<211> LENGTH: 18
<212> TYPE: DNA
<213> ORGANISM: Artificial Sequence
<220> FEATURE:
<223> OTHER INFORMATION: Primer
```

```
<400> SEQUENCE: 45
atggcccaat ggaatcag                                                  18

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
tcacatgggg gaggtagc                                                  18

<210> SEQ ID NO 47
<211> LENGTH: 6
<212> TYPE: PRT
<213> ORGANISM: Artificial Sequence
<220> FEATURE:
<223> OTHER INFORMATION: Peptide

<400> SEQUENCE: 47

Cys Cys Pro Gly Cys Cys
1               5
```

METHODS AND SYSTEMS FOR IDENTIFYING PATIENT SPECIFIC DRIVER MUTATIONS

CROSS-REFERENCE TO RELATED APPLICATIONS

This application is a continuation of U.S. patent application Ser. No. 14/761,002, filed Jul. 14, 2015, (now allowed), which is a 371 US national stage entry of International Patent Application No. PCT/IL2014/050054, filed Jan. 16, 2014, which claims the benefit of priority of U.S. Provisional Patent Application No. 61/753,458, filed Jan. 17, 2013, which are hereby incorporated by reference their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NODX_003_02US_SeqList_ST25.TXT, date recorded Jul. 10, 2018, file size 9 kilobytes).

FIELD OF THE INVENTION

Methods for identifying patient specific driver mutations are provided. The methods provided identify specific patient derived markers associated with aberrant signal transduction pathways, in biological samples of a cancer patient.

BACKGROUND OF THE INVENTION

Clinical therapeutic protocol and prognosis of patients diagnosed with various disease conditions, such as cancer, may be drastically different depending on accurate diagnosis of underlying molecular mechanism as well as identification of all driver mutations and auto and paracrine effects. In addition, many diseases that may be phenotypically (pathologically) similar can have very different underlying causes. Cancers, for example, are extremely diverse; therefore, accurate diagnosis and stratified therapeutic approaches are critical for effective treatment. In patients diagnosed with cancer, many of the signaling pathways that control cell growth and differentiation are regulated in an abnormal fashion, particularly the balance between cell proliferation and cell death. Many of these pathways are activated due to the accumulation of mutations in key proteins, termed "driver mutations" or due to the secretion of growth factors and cytokines by tumor cells or stromal cells and reactivation of receptors on the tumor plasma membrane that activates these signaling pathways. These mutations encompass a wide range of processes but all share the ability to endow the cells with oncogenic activity. Hence, targeting such driver mutations with specific inhibitory drugs ("targeted therapy") is a main goal in cancer therapy. For example, lung cancer may possess many underlying participating factors (e.g. EGFR mutations and the ALK-ELM4 translocation) each of which require a different therapeutic approach. Likewise, the treatment of breast cancer is dictated by the underlying molecular profile (such as ER/PR expression or HER2 amplification). The interplay between the different pathways is highly complex and is tumor-specific and in most cases patient specific. Full understanding of the patient specific tumor underlying signaling mechanism is required to determine the best combination of targeted therapy drugs are likely to be effective by interrupting the aberrant signaling pathways to inhibit cell division and induce cell death. The heterogeneity of tumors (genetic polymorphism) among individuals has a profound impact on drug efficacy as well as the likelihood of undesirable off-target side effects and ultimately the survival rate.

Among some 320 known signaling pathways in humans, about 50 signaling pathways are directly or indirectly involved in tumor growth and progression. There is an unmet need for a platform that enables the identification of the profile of the patient's tumor activated signaling pathways by monitoring the activation of various signaling proteins (such as, for example, membrane-localized and/or intracellular receptors and signaling proteins), in viable test cells.

The complexity and heterogeneity of cancer demands a more sensitive and discerning diagnostic approach that mirrors the tumor signaling pathway in a qualitative and quantitative manner and enables accurate selection of stratified therapy. The current state of the art is that few individual markers can be used to predict drug efficacy and toxicity. Moreover, the suitability of whole-genome sequencing (next generation sequencing) for selection of targeted therapy is limited due to the large pool of mutations accumulating within the tumor and the limited repertoire of identified driver mutations. In addition, whole-genome sequencing does not reveal auto and paracrine stimulation which are major drivers in tumor proliferation.

Thus, there is unmet need in the art for methods and systems that provide for a patient specific diagnostic platform, which is both cost and time effective, and which have the ability to specifically identify patient specific driver mutations and auto-paracrine mutations based on their aberrant activity and can consequently predict a specific, personalized and optimized treatment.

SUMMARY OF THE INVENTION

The present invention provides methods and systems for identifying patient specific driver mutations, by identifying changes in signaling pathway activity, which is associated with the function of the driver mutation, in a test cell. According to some embodiments, changes in the signaling pathway activity are determined by identifying changes in subcellular localization of a reporter gene, which is associated with the function of the driver mutation. In some embodiments, specific patient derived marker (PDM) genes are obtained from a biological sample, and their effect on the subcellular translocation of a corresponding fluorescent translocation reporter (FIR) gene is tested in viable test cells, to determine whether the tested PDM is mutated. In some embodiments, the specific patient derived marker is obtained and fused to a fluorescent reporter to create a patient derived reporter (PDR), wherein the subcellular translocation of the PDR is tested in viable test cells, to determine whether the tested PDR is mutated.

The methods and systems disclosed herein further allow the determination of the intracellular pathways associated with a disease in general, and of the specific components of the signaling pathways, which are aberrantly affected. The analysis provided by the methods and systems disclosed herein further allow determining and/or adjusting an optimal personalized treatment adapted to the thus identified patient specific driver mutations.

In some embodiments, the present invention provides methods and systems for identifying patient specific driver mutations involved in cancer. In some embodiments, the driver mutations are oncogenic driver mutations. In some embodiments, the methods and systems provide a predictive platform to test the effect of various paracrine and autocrine factors on the specific cancer and its progression. In some embodiments, the methods and systems provide a predictive platform to determine the effect of a tested drug or combination of drugs on the patient specific cellular pathways. In some embodiments, the methods and systems provide a predictive platform to determine an optimized treatment specifically adjusted to the patient. In some embodiments, the methods disclosed herein enable the identification of auto and paracrine effects on cellular and intercellular signaling pathways. In some embodiments, the methods disclosed herein enable the detection and/or prediction of inherent and acquired drug resistance mechanisms.

According to some embodiments, there is provided a method for identifying patient specific driver mutations by identifying changes in subcellular localization of a reporter marker gene, whereby the changes in the subcellular localization are affected by the driver mutation. In some embodiments, patient derived markers (PDMs) are obtained from biological sample of the patient, and are manipulated (engineered) to be expressed in a viable test cell, in the presence of a reporter chimeric gene (Fluorescence Translocation Reporter (FTR), comprising a chimeric product of a reporter gene portion and a target gene portion). The subcellular localization of the FTR in the test cell is then determined. If the subcellular localization of the FTR in the presence of the tested PDM is different than the subcellular localization of the FTR under normal conditions (i.e. in the presence of a corresponding WT PDM) and/or as compared to other known reference, it is indicative that the tested PDM is mutated. Thus, using the methods disclosed herein, patient specific PDMs can be identified/characterized as being driver mutations. Alternatively or additionally, in some embodiments, a PDM can be tested directly, by creating a PDR (i.e. a PDM linked/attached/fused to a reporter gene), and tracking its subcellular localization, without the use of FTR. Moreover, by determining such driver mutations, the activated signaling pathways operating within the patient tumor can be identified. Further, this enables to precisely and specifically choose the required targeted therapy treatment needed to eradicate the tumor and avoid resistance mechanisms of the specific patient.

According to some embodiments, there is advantageously provided a novel diagnostic platform for personalized cancer therapy based on biological sample obtained from the tumor tissue. In some embodiments, the method is a cell-based assay that is able to sense such activating-driver mutations by monitoring their effect on an FTR in live (viable) cells, immobilized on substrate, and specifically, their ability to activate signaling pathways known to be involved in tumor development. In some embodiments, this may be performed by detecting intracellular translocation events and protein-protein interactions involving fluorescent reporter proteins (FTRs) (that is, translocation to/between various subcellular localizations, such as, the plasma membrane, cytosol, endosomes, nucleus, and the like). Thus, the methods and systems disclosed herein can allow the identification of such cellular events prior to first line treatment, thereby driving an effective treatment regime. Additionally, over growth of tumor resistant cells stimulation by drug treatment may be prevented.

According to some embodiments, there is thus provided a method of identifying one or more patient specific driver mutations in a biological sample of a cancer patient, comprising the steps of:

a) obtaining a plurality of mRNAs from the biological sample;

b) generating a cDNA library from the plurality of mRNAs;

c) amplifying specific cDNAs of the cDNA library using a set of primers complementary to polynucleotides encoding for known signal transduction proteins;

d) forming individual expression constructs of the amplified cDNAs wherein the cDNAs are operably linked to a promoter;

e) forming an addressable array of a first set of expression constructs harboring the amplified cDNAs from the tumor, and a second set of expression constructs of the corresponding wild type cDNAs;

thereby providing an addressable array of expression constructs harboring candidate mutations in polynucleotides encoding for the signal transduction proteins, the array is suitable for identifying patient specific driver mutations in a biological sample of the cancer patient.

In some embodiments, the method further comprises a step (f) of adding an expression vector encoding for a Fluorescence Translocation Reporter (FTR) gene comprising a target gene portion linked to a specific reporter gene portion for each locus in the array.

In further embodiments, the method further comprises the steps of: (g) adding viable assay cells to each locus under conditions enabling transfection of the DNA constructs and vectors into the assay cells; and (h) comparing at least one attribute of the expressed FTR in the assay cells expressing the cDNAs from the tumor with its corresponding wild type expressed cDNAs; wherein a disparate result between the assay cells expressing the cDNA derived from the biological sample of the cancer patient and the corresponding wild type cDNA, is used for identifying the cDNA from the biological sample as a candidate patient specific driver mutation.

In some embodiments, the attribute of the FTR is selected from localization of a fluorescent protein and translocation of a fluorescent protein. In some embodiments, the localization comprises a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor. In further embodiments, the reporter gene portion of the FTR encodes for: Green Fluorescent Protein (GFP), mCherry, mApple, DsRed, Red Fluorescent Protein (RFP), Blue Fluorescent Protein (BFP), EGFP, CFP, YFP, AmCyan1, ZsGreen1, ZsYellow1, DsRed2, AsRed2, and HcRed1.

In some embodiments, the biological sample is selected from tumor cells, tumor biopsy, tumor tissue and bodily fluids.

In some embodiments, the first and/or second sets of expression constructs comprise a double stranded linear DNA. In other embodiments, the promoter of the first and/or second set of expression constructs is an inducible promoter. In some embodiments, the promoter of the first and/or second set of expression constructs is a constitutive promoter.

In some embodiments, the method further comprises inducing expression of the expression construct and/or expression vector in the transfected cells to obtain gene products of the first set of cDNAs from the tumor and the FTR for each locus in the array.

In further embodiments the expression constructs of the amplified cDNAs further comprise an IRES and a second reporter gene.

In some embodiments, the method further comprises drying the DNA constructs on a solid support in the presence of a transfection reagent.

According to some embodiments, there is provided a method of identifying aberrant signal transduction pathways in tumor cells, comprising the steps of:
 a) obtaining a plurality of mRNAs from the tumor cells;
 b) generating a cDNA library from the plurality of mRNAs;
 c) amplifying specific cDNAs of the cDNA library using a set of primers complementary to polynucleotides encoding for known signal transduction proteins;
 d) forming individual expression constructs of the amplified cDNAs of step (c), wherein the cDNAs are operably linked to a promoter;
 e) forming an addressable array of a first set of expression constructs harboring the amplified cDNAs from the tumor, and a second set of expression constructs of the corresponding wild type cDNAs;
 thereby providing an addressable array of expression constructs harboring candidate mutations in the polynucleotides encoding for the signal transduction proteins, suitable for identifying aberrant signal transduction pathways in the tumor cells.

In some embodiments, the method further comprises a step (f) of adding an expression vector encoding for a Fluorescence Translocation Reporter (FTR) gene comprising a target gene portion linked to a reporter gene portion, for each locus in the array.

In additional embodiments, the method further comprises the steps of: g) adding viable assay cells to each locus under conditions enabling co-transfection of the DNA constructs into the assay cells; and h) comparing at least one attribute of the expressed FTR in the assay cells expressing the cDNAs from the tumor with its corresponding wild type expressed cDNAs; wherein a disparate result between the assay cells expressing cDNA derived from the tumor cells and the corresponding wild type cDNA is used for identifying the cDNA from the tumor cells as a candidate aberrant signal transduction protein.

In some embodiments, the tumor cells are derived from a tumor sample of a cancer patient, said tumor sample selected from: biopsy, tumor section following surgery, blood sample, Bronchoalveolar lavage, and bone marrow.

In further embodiments, a candidate aberrant signal transduction protein identified by the method is a patient specific driver mutation.

According to some embodiments, there is provided a method of identifying one or more patient specific driver mutations in a biological sample of a cancer patient, comprising the steps of:
 a) obtaining a plurality of mRNAs from the biological sample;
 b) generating a cDNA library from the plurality of mRNAs;
 c) amplifying specific cDNAs of the cDNA library using a set of primers complementary to polynucleotides encoding for known signal transduction proteins;
 d) forming individual expression constructs of the amplified cDNAs wherein the cDNAs are operably linked to a promoter;
 e) adding viable assay cells to a substrate, in an addressable array;
 f) adding to the assay cells a first set of expression constructs harboring the amplified cDNAs from the tumor, and a second set of expression constructs of the corresponding wild type cDNAs; wherein each of the expression constructs is added to the assay cells at a disparate, addressable locus, under conditions enabling transfection of the expression constructs into the assay cells;
 thereby generating an array of assay cells comprising expression constructs harboring candidate mutations in polynucleotides encoding for signal transduction proteins, suitable for identifying patient specific driver mutation in a biological sample of the cancer patient.

In some embodiments, the method further comprises a step of adding to the assay cells an expression vector of a Fluorescence Translocation Reporter (FTR) gene comprising a target gene portion linked to a specific reporter gene portion for each locus in the array.

In some embodiments, the method further comprises comparing at least one attribute of the FTR in the cells expressing the cDNAs from the tumor with its corresponding wild type expressed cDNAs; wherein a disparate result between the assay cells expressing the biological sample derived cDNA and the corresponding wild type cDNA is used for identifying the cDNA from the biological sample as a candidate patient specific driver mutation.

In some embodiments, the biological sample is selected from tumor cells, tumor biopsy, tumor tissue and bodily fluids.

According to some embodiments, there is provided a method of identifying aberrant signal transduction pathways in tumor cells, comprising one or more of the steps of:
 a) obtaining a plurality of mRNAs from a tumor sample;
 b) generating a cDNA library from the plurality of mRNAs;
 c) amplifying specific cDNAs of the cDNA library using a set of primers complementary to polynucleotides (genes or gene portions) of known signal transduction proteins;
 d) forming individual expression constructs of the amplified cDNAs of (c) wherein the cDNAs are operably linked to a promoter;
 e) forming an addressable array of a first set of expression constructs harboring the amplified cDNAs from the tumor, and a second set of expression constructs of the corresponding wild type cDNAs;
 f) adding an expression vector for co-transfection of a Fluorescence Translocation Reporter (FTR) chimeric gene comprising a target gene portion linked to a reporter gene portion, for each locus in the array;
 g) adding viable assay cells to each locus under conditions enabling transfection of the DNA constructs into the assay cells;
 h) comparing at least one attribute of the expressed FTR in the cells expressing the cDNAs from the tumor with its corresponding wild type expressed cDNA;
 wherein a disparate result between the cells expressing tumor derived cDNA and the corresponding wild type cDNA is used for identifying the cDNA from the tumor as a candidate aberrant signal transduction protein.

In some embodiments, the attribute of the reporter gene is selected from the localization of a fluorescent protein and translocation of a fluorescent protein.

In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor.

In some embodiments, the reporter gene portion of the FIR encodes for or is selected from: Green Fluorescent Protein (GFP), mCherry, mApple, DsRed, Red Fluorescent Protein (RFP), Blue Fluorescent Protein (BFP), Enhanced Green Fluorescent Protein (EGFP), Cyan Fluorescent Protein (CFP), Yellow Fluorescent Protein (Y FP), AmCyan1, ZsGreen1, ZsYellow1, DsRed2, AsRed2, and HcRed1.

According to additional embodiments, the localization comprises a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the first and/or second expression constructs comprises a double stranded linear DNA. In further embodiments, the promoter of the first and/or second expression constructs is an inducible promoter. In some embodiments, the promoter of the expression construct is a constitutive promoter.

In some embodiments, the expression constructs of the amplified cDNAs further comprises an IRES and a second reporter gene.

In some embodiments, the expression vector of the FTR is a circular expression vector. In further embodiments, the expression vector comprises a constitutive or inducible promoter.

In some embodiments, step g) precedes steps e) and/or f), in which case the assay cells are added to each locus, prior to addition of expression constructs and/or expression vectors.

In some embodiments, the method further comprises drying the DNA constructs on a solid support in the presence of a transfection reagent.

According to some embodiments, the assay cell is selected from HeLa cells, HEK 293 cells, U2OS, PC12, A549, EKVX, T47D, HT29 and a cell of a patient.

According to further embodiments, a candidate aberrant protein identified by the method is a patient specific driver mutation.

In additional embodiments, the cells are obtained from a biological sample of a cancer patient. In some embodiments, the tumor sample is selected from biopsy, tumor section following surgery, blood sample, Bronchoalveolar lavage, and bone marrow.

In some embodiments, the method further comprises expressing the constructs and/or the expression vector in the transfected cells to obtain gene products of the first set of cDNAs from the tumor and the FTR for each locus in the array.

According to some embodiments, there is provided a method of identifying patient specific driver mutations in biological sample of a cancer patient, comprising the steps of:

a. obtaining a sample of plurality of mRNA from the biological sample;

b. generating a cDNA library from the plurality of mRNAs;

c. amplifying individual cDNA samples of the cDNA library using a set of primers complementary to polynucleotides encoding for known signal transduction proteins;

d. forming individual expression constructs of the amplified cDNAs wherein the cDNAs are operably linked to a promoter;

e. forming an addressable array of a first set of expression constructs harboring the amplified cDNAs from the tumor, and in parallel a second set of expression constructs of the corresponding wild type cDNAs;

f. adding an expression vector for co-transfection of a Fluorescence Translocation Reporter (FTR) gene comprising a target gene linked to a specific reporter gene for each locus in the array;

g. adding viable assay cells to each locus under conditions enabling transfection of the DNA constructs into the assay cells;

h. comparing at least one attribute of the reporter gene in the cells expressing the cDNAs from the tumor with its corresponding wild type expressed cDNA;

wherein a disparate result between the cells expressing the biological sample derived cDNA and the corresponding wild type cDNA is used for identifying the cDNA from the biological sample as a candidate patient specific driver mutation.

In some embodiments, the biological sample is selected from a tumor cell, a tissue, a biopsy, and a bodily fluid.

In some embodiments, the cellular proteins can be any type of cellular protein which may be related to a cancer condition. In some embodiments, the cellular proteins may be involved in various cellular processes. In some embodiments, the cellular proteins may be selected from, but not limited to: proteins involved in signal transduction pathways, cytoskeleton proteins, enzymes, proteins involved in translation, protein involved in cell cycle regulation, proteins involved in transcription, proteins involved in metabolism, and the like, or combinations thereof.

According to some embodiments, there is further provided a kit for identifying patient specific driver mutations in biological sample of a cancer patient. In further embodiments, there is provided a kit for identifying aberrant signal transduction pathways in tumor cells of a patient.

BRIEF DESCRIPTION OF THE DRAWINGS

FIG. 3B—A schematic representation of the signaling pathway affected by the PDM (KRAS) and the corresponding FTR (ERK2).

FIG. 4B—A schematic representation of the signaling pathway affected by the PDM (KRAS) and the corresponding FTR (ERF).

FIG. 5B—A schematic representation of the signaling pathway affected by the PDM (KRAS) and the corresponding FTR (JNK1a1).

FIG. 6B—A schematic representation of the signaling pathway affected by the PDM (KRAS) and the corresponding FTR (AKT1).

FIG. 7B—A schematic representation of the signaling pathway affected by the PDM (AKT2) and the corresponding FTR (AKT1).

FIG. 8B—A schematic representation of the signaling pathway affected by the PDM (AKT2) and the corresponding FTR (RelA).

FIG. 9B—A schematic representation of the signaling pathway affected by the PDM (AKT3) and the corresponding FTR (AKT1).

FIG. 10B—A schematic representation of the signaling pathway affected by the PDM (AKT3) and the corresponding FTR (RelA).

FIG. 11B—A schematic representation of the signaling pathway affected by the patient derived reporter (PDR), SMAD2.

FIG. 12B—A schematic representation of the signaling pathway affected by the PDM (FGFR1) and the corresponding FTR (ERK2).

FIG. 13B—A schematic representation of the signaling pathway affected by the PDM (FGFR1) and the corresponding FTR (JNK1a1).

FIG. 14B—A schematic representation of the signaling pathway affected by the PDM (FGFR1) and the corresponding FTR (P38b).

FIG. 15B—A schematic representation of the signaling pathway affected by the PDM (FGFR1) and the corresponding FTR (STAT3).

FIG. 16B—A schematic representation of the signaling pathway affected by the PDM (FGFR1) and the corresponding FTR (AKT).

FIG. 17B—A schematic representation of the signaling pathway affected by the PDM (BRAF) and the corresponding FTR (ERK2).

FIG. 18B—A schematic representation of the signaling pathway affected by the PDM (BRAF) and the corresponding FTR (ERK).

FIG. 19B—A schematic representation of the signaling pathway affected by PDM (EGFR) 10 and the corresponding FTR (RelA).

FIG. 20B—A schematic representation of the signaling pathway affected by PDM (EGFR) and the corresponding FTR (AKT1).

FIG. 21B—A schematic representation of the signaling pathway affected by PDM (EGFR) 30 and the corresponding FTR (JNK1A1).

FIG. 22B—A schematic representation of the signaling pathway affected by PDM (EGFR) and the corresponding FTR (P38b).

FIG. 23B—A schematic representation of the signaling pathway affected by PDM (EGFR) and the corresponding FTR (ERK2).

DETAILED DESCRIPTION OF THE INVENTION

Figure 1:
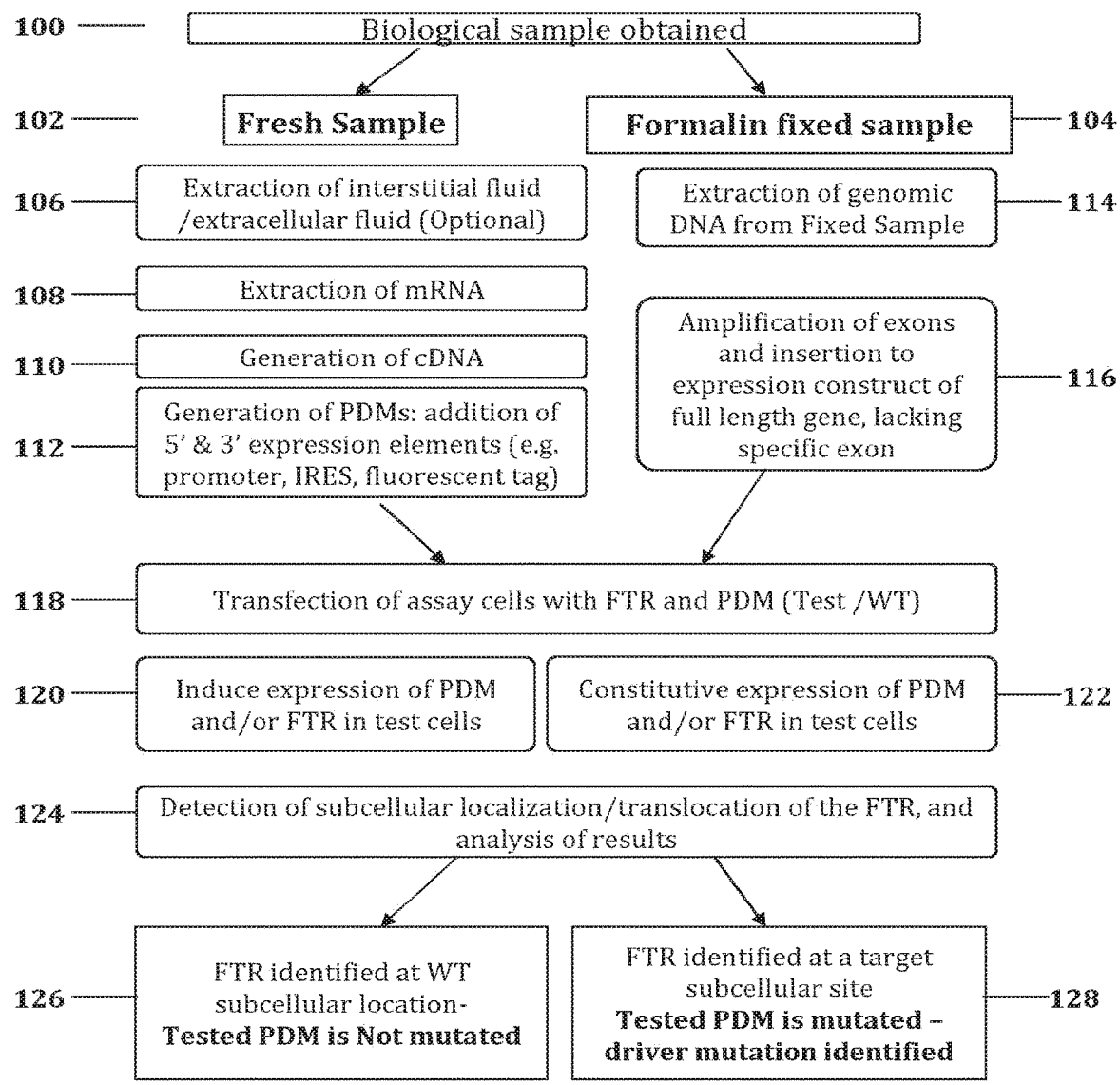
FIG. 1 is a schematic block diagram of steps of a method for obtaining patient derived markers and identification of driver mutations, according to some embodiments.

According to some embodiments, there is provided a method for identifying patient specific driver mutations by identifying changes in signaling pathway activity, which is associated with the function of the driver mutation. In some embodiments, the changes in the signaling pathway activity are determined by identifying changes in subcellular localization of a reporter gene, whereby the changes in the subcellular localization of the reporter gene are affected by the driver mutation. In some embodiments, patient derived markers (PDMs) are obtained from biological sample of the patient, and are manipulated (engineered) to be expressed in a test cell, in the presence of a reporter chimeric gene (FTR). In some embodiments, additionally or alternatively, the patient specific marker is fused to the fluorescent reporter to create a patient derived reporter (PDR). The subcellular localization of the FTR (and/or PDR, if applicable) in the test cell is then determined If the subcellular localization of the FTR in the presence of the tested PDM (and/or the PDR, if applicable) is different than the subcellular localization of the FTR (and/or PDR, if applicable) under normal conditions (i.e. in the presence of a corresponding WT PDM) or as compared to other predetermined reference, it is indicative that the tested PDM (or PDR) is mutated. Thus, using the methods disclosed herein, patient specific PDMs can be identified/characterized as being driver mutations. Moreover, by determining such driver mutations, the activated signaling pathways operating within the patient tumor can be identified. Further, this may enable to precisely and specifically choose the required targeted therapy treatment needed to eradicate the tumor and avoid resistance mechanisms of the specific patient. In some embodiments, the methods provided herein provide a fine-grained resolution of a tested signaling system in a biological sample, and can accurately monitor the activity level of multiple pathways involved therewith.

In some embodiments, the invention is based on the notion that proteins involved in cancer signaling pathways translocate in response to various environmental factors, thereby, by testing the localization of chimeric reporter genes, that are affected by such signaling pathways, patient specific driver mutations can be identified. According to some embodiments, the methods and systems disclosed herein are advantageous since although there is a vast amount of information regarding oncogenic mutations, robust methods and systems for identifying multiple mutation events in the same biological sample of the same patient, as well as not yet unidentified mutations, as disclosed herein, and determination of the oncogenic activity of such mutations, are not previously available. For example, in currently used methods of treatment, gastrointestinal stromal tumor patients harboring cKit mutations, are treated with Gleevec. However, common resistance mechanisms occur through secondary mutations within cKit itself or in downstream pathways, rendering such treatment ineffective. Likewise, colorectal cancer patients that have over-expression of the EGFR oncogene are eligible for Cetuximab treatment, but only in the presence of a normal form of the KRAS oncoprotein.

In some embodiments, the methods and systems disclosed herein enable the emulation of the patient tumor to identify activated signaling pathways as well as identify oncogenic activity. In addition, the methods can be used to predict tumor sensitivity/resistance to anti-cancer therapy. In some embodiments, this is performed by incubating the transfected test cells with the patient body fluids (such as plasma, pleural effusion, or interstitial fluid).

As referred to herein, the terms "polynucleotide molecules", "oligonucleotide", "polynucleotide", "nucleic acid" and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucicotide or polynucicotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions.

The term "construct", as used herein refers to an artificially assembled or isolated nucleic acid molecule which may include one or more nucleic acid sequences, wherein the nucleic acid sequences may include coding sequences (that is, sequence which encodes for an end product), regulatory sequences, non-coding sequences, or any combination thereof. The term construct includes, for example, vectors but should not be seen as being limited thereto.

The term "Expression vector" refers to vectors that have the ability to incorporate and express heterologous nucleic acid fragments (such as DNA) in a target cell. In other words, an expression vector comprises nucleic acid sequences/fragments capable of being transcribed. Many viral, prokaryotic and eukaryotic expression vectors are known and/or commercially available. Selection of appropriate expression vectors is within the knowledge of those having skill in the art.

The terms "Upstream" and "Downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

The terms "promoter element", "promoter" or "promoter sequence" as used herein, refer to a nucleotide sequence that is generally located at the 5' end (that is, precedes, located upstream) of the coding sequence and functions as a switch, activating the expression of a coding sequence. If the coding sequence is activated, it is said to be transcribed. Transcription generally involves the synthesis of an RNA molecule (such as, for example, a mRNA) from a coding sequence. The promoter, therefore, serves as a transcriptional regulatory element and also provides a site for initiation of transcription of the coding sequence into mRNA. Promoters may be derived in their entirety from a native source, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions, or at various expression levels. Promoters which cause a gene to be expressed in most cell types at most times are commonly referred to as "constitutive promoters". Promoters that derive gene expression in a specific tissue are called "tissue specific promoters".

As used herein, the terms "introducing" and "transfection" may interchangeably be used and refer to the transfer or introduction of molecules, such as, for example, nucleic acids, polynucleotide molecules, vectors, and the like into a target cell(s), and more specifically into the interior of a membrane-enclosed space of a target cell(s), such as the cytosol of a cell, the nucleus of a cell, an interior space of a mitochondria, endoplasmic reticulum (ER), and the like. The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. In some embodiments, the introduced nucleic acid may be, for example, a modified nucleic acid that may be in the form of DNA, RNA. In some embodiments, the nucleic acid is dehydrated prior to being transfected to a cell. In some embodiments, the nucleic acid is incorporated into a vector, such as, for example, an expression vector. Each possibility represents a separate embodiment of the present invention.

The term "expression", as used herein, refers to the production of a desired end-product molecule in a target cell. The end-product molecule may include, for example an RNA molecule; a peptide or a protein; and the like; or combinations thereof.

As referred to herein, the term "patient" is directed to a subject having or diagnosed with cancer. In some embodiments, a patient is eligible for tumor biopsy.

As referred to herein, the term "biological sample" is directed to include any appropriate body-derived sample. The sample may include fluid samples such as whole blood, peripheral blood monocytes, leukocytes, bone marrow. The samples may include various cells and tissues. The sample may include biopsies. The sample may include fixed and/or embedded tissue sections. The samples may be either freshly extracted or frozen. In another embodiment, the sample is a blood sample. In another embodiment, the sample is a bone marrow sample. In another embodiment, methods for isolating and maintaining a sample comprising blood cells from a subject are known to one of average skill in the art. In some embodiments, a sample comprising polynucleotides, polypeptides, peptides, antibodies fragments and derivatives thereof may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; fragments and derivatives thereof. In some embodiments, the biological simple is obtained from a tumor.

As referred to herein, the terms "Patient Derived Marker" ("PDM"), and "subject PDM" are directed to a gene or gene product that is isolated from a biological sample of the subject and its activity in a functional assay is determined In some embodiments, to the PDM nucleic acid sequence, which is obtained from the biological sample, 5' and/or 3' regulatory elements and/or additional reporter genes are added. In some examples, a PDM as used herein comprises a chimeric nucleic acid sequence molecule comprising a 5' regulatory element (promoter)—the PDM sequence-3' regulatory element (IRES)-reporter gene. Thus, when such a nucleic acid molecule is introduced and expressed in a target cell, the PDM gene product (protein) and the reporter gene product (protein) are expressed in the cell. Additionally or alternatively, an IRES sequence can be omitted and a chimeric protein comprising the PDM gene product and the reporter gene product is expressed in the cell. The thus formed chimeric protein is referred to herein as "Patient Derived Reporter" ("PDR"), or "subject PDR". If the tested PDM is found to be mutated by the functional assay, it may be considered as a driver mutation. In some embodiments, the terms "control PDM", "wild type PDM", "corresponding PDM" and "corresponding wild type PDM" are directed to a wild type gene corresponding to the PDM gene (i.e. a non-mutated, fully active), that is used as control. In some embodiments, the wild type PDM is not derived from a biological sample of the patient. The control PDM is used to compare the activity of the subject PDM and the wild type (wt) PDM.

As referred to herein, the term "Fluorescence Translocation Reporter" ("FTR") is directed to a chimeric reporter gene and the corresponding gene product. The chimeric FTR comprising a reporter gene portion (such as a fluorescent protein) linked to a predetermined target (marker) gene portion (such as, for example, a cell signaling protein, kinase, enzyme, and the like), whereby at least one attribute of the target (marker) gene may be affected (directly or indirectly) by the tested PDM.

As referred to herein, the terms "test cell", "target cell" and "assay cell" may interchangeably be used. The terms are directed to an assay cell which is transfected with a poly nucleic acid molecule such as PDM and/or PDR and/or FTR and/or any of control genes, as described herein. In some embodiments, the test cell is an eukaryotic cell. In some embodiments, the test cell may be a primary cell or a cell line. In another embodiment, an assay cell is a non-cancerous cell. In another embodiment, an assay cell is derived from a cell line. In another embodiment, an assay cell is responsive to at least one cancer-secreted growth factor. In another embodiment, an assay cell is amenable by transfection. In another embodiment, an assay cell is amenable by transient transfection. In another embodiment, an assay cell is a cell, in which the expression of one or more endogenous genes have been reduced or eliminated by any molecular method. In another embodiment, an assay cell is Hela cell. In another embodiment, an assay cell is HEK 293 cell. In another embodiment, an assay cell is PC12 cell. In another embodiment, an assay cell is U2OS cell. In another embodiment, an assay cell is NCI60 cell lines, such as, A549, EKVX, T47D, HT29. In some embodiments, the assay cell is a cell derived from the patient. In some embodiments, the assay cell is a cell derived from a cancer patient.

As used herein, the terms "subcellular localization", "subcellular region" and "subcellular compartment" refer to any defined part of a cell that may be distinguished by various means (such as, for example, by visual means) from other regions of the cell. In some examples, a subcellular region may be a restricted area within a cell. In some embodiments, a subcellular region may include an organelle. Non limiting examples of subcellular localization include, for example, but not limited to: nucleus, nucleolus, cytosol, mitochondria, endoplasmic reticulum (ER), chloroplasts, membranes, dendritic spines, Golgi apparatus, lysosomes, peroxisomes, endosomal compartments, cytoskeleton, and the like. In some embodiments, the term "subcellular translocation" refers to a detected change in the subcellular localization of a reporter gene (such as, FIR or PDR) under various conditions.

As referred to herein, the term "drug" is directed to a compound that has an effect in treating of a condition. The terms "Treating a disease" or "treating a condition" is directed to administering of one or more compounds, effective to ameliorate symptoms associated with a disease, to lessen the severity or cure the disease, or to prevent the disease from occurring.

The terms "Detection, "Diagnosis" refer to methods of detection of a disease, symptom, disorder, pathological or normal condition; classifying a disease, symptom, disorder, pathological condition; determining a severity of a disease, symptom, disorder, pathological condition; monitoring disease, symptom, disorder, pathological condition progression; forecasting an outcome and/or prospects of recovery thereof. The term "Diagnostic" means identifying the presence or nature of a pathologic condition.

The term "substrate" is directed to a solid support on which the nucleic acid molecules, constructs, vectors and/or assay cells are placed. The substrate may include any type of suitable substrate, such as, but not limited to: chip, slide, well, container, tube, vial, and the like. In some embodiments, the substrate is a chip. In some embodiments, the substrate is a microscope slide. In some embodiments the substrate is a multi-well plate, such as a 6-well plate, 12-well plate, 24-well plate, 48-well plate, 96 well plate, 384 well plate, and the like. In some embodiments, the substrate is constructed such that it includes a matrix array (locuses), whereby each locus (or point in the array) is designated and identifiable. In some embodiments, the nucleic acid molecules are dehydrated on the substrate. In some embodiments, the nucleic acid molecules are dehydrated on the substrate in the presence or absence of a transfection reagent.

The term "driver mutation" is directed to a mutated gene or gene product, which can lead or cause a disease, such as cancer.

The term "polynucleotides encoding for a protein" refers to a polynucleotide sequence or molecule encoding for the corresponding protein or a portion thereof. In some embodiments, the polynucleotide encoding for a protein comprises the nucleotide sequence of the gene or a portion thereof, which encodes for the corresponding protein.

Reference is now made to FIG. 1, which schematically illustrates a block diagram of exemplary steps in a method for identifying patient specific driver mutations, in a biological sample of a patient, according to some embodiments. As shown in FIG. 1, at step 100, a biological sample of the patient is obtained. The biological sample may be selected from, but not limited to: blood, serum, biopsy, needle biopsy, bronchoalveolar lavage, pleural effusion, tumor tissue, urine, saliva and tumor tissue. In some embodiments, the biological sample may be fresh (fresh or freshly frozen), i.e. samples which are not fixed (step 102). In some embodiments, the biological sample may be fixed, by methods know in the art for fixation of biological sample (Step 104).

As shown in FIG. 1, from a fresh biological sample (Step 102), various components may be extracted, each by appropriate methods well known in the art. For example, as shown in Step 106, interstitial fluid (IF) (extracellular fluid) may be extracted and saved for future use. Additionally, mRNA may be extracted from the fresh biological sample (Step 108). The extracted/isolated mRNA is then used for the generation of cDNA libraries (Step 110), by methods well known in the art (such as, by using polydT primers). Specific PDM cDNAs are amplified from the cDNA library and created by using appropriate primer pairs, corresponding to desired gene regions (polynucleotides) of predetermined PDMs. The selected PDMs, may be chosen based on the known function/activity/role of a corresponding WT PDM or mutated PDM in various disease states (for example, oncogenes). Next, at step 112, an assay PDM is created, by adding a regulating promoter element to the 5' end of the PDM cDNA, and optionally adding a 3' IRES and a tag, such as a reporter gene, fluorescent tag, and the like. In some embodiments, the promoter element may be a constitutive promoter or an inducible promoter. In some embodiments, the PDM cDNA may further include an additional expression cassette which includes an FTR encoding portion.

As further shown in FIG. 1, at step 114, genomic DNA may be extracted from a fixed biological sample (such as a formalin fixed sample (Step 104)). At step 116, the extracted DNA may undergo amplification of specific, predetermined exons (which are known to be mutated in cancer cases) and consequent ligation/fusion to expression constructs comprising the corresponding full length gene, lacking the specific exons amplified to generate a tested PDM.

Next, in step 118, the nucleic acid molecule of each of the PDMs generated in step 112 and/or step 116 may be placed/spotted on a support substrate (such as, a slide, well (for example, microplate well), chip, and the like) at a designated locus (location). The PDM is placed in a mixture with a nucleic acid molecule encoding for the chimeric reporter (FTR), wherein the FTR is selected to correspond to the PDM (i.e., the selected FTR may be functionally affected (directly or indirectly) by the PDM). The mixture of the nucleic acid molecules encoding for the PDM and the FTR may further comprise appropriate transfection reagents to allow the transfection of the molecules to a test cell. Optionally, the PDM+FTR mixtures are dehydrated onto the substrate. In another option, the PDM and FTR are constructed to be located on a single nucleic acid molecule, allowing independent expression of both proteins in the cell. In parallel, a control assay is prepared, which comprises a WT PDM and a corresponding FTR. Further in step 118, a sufficient amount of selected test cells are added to the substrate, together with appropriate growth media. The cells may be added prior to or after the addition of the nucleic acid molecules. In some embodiments, a sufficient amount of test cells comprises about 1-10000 cells per well (96 multi-plate well). In some embodiments, a sufficient amount of test cells comprises about 1-50000 cells per well (24 multi-plate well). In some embodiments, a sufficient amount of test cells comprises about 1-100000 cells per well (12 multi-plate well). In some embodiments, a sufficient amount of test cells comprises about 1-1000 cells per well (96 multi-plate well). In some embodiments, a sufficient amount of test cells comprises about 1-1000 cells per well (384 multi-plate well). In some embodiments, the test cell is selected from, but not limited to: HeLa cells, HEK 293 cells, U205, PC12, NCI60, A549, EKVX, T47D, HT29, and the like. The cells are then incubated for a designated period of time (such as, in the range of about 6-60 hours) to allow expression of the FTR and optionally of the PDM.

Optionally, in some embodiments, in step 118, the cells are added to the solid substrate (with a suitable growth medium) for a period of time (such as 0.5-48 hours) and then the nucleic acid molecules encoding for the PDMs and/or FTR are added to the cells, under conditions allowing transfection of the molecules into the cells.

Next, at step 120, after a predetermined period of time (such as, 4-60 hours), cell growth medium may be replaced with fresh media. In some embodiments, the replacement media is low serum media. Next, after an additional incubation period (such as, in the range of 4-16 hours), induction of the expression of the PDM, controlled by an inducible promoter is initiated. Induction of the inducible promoter may be initiated, for example by addition of tetracycline when using a tetracycline inducible promoter, or ecdysone when using in an ecdysone inducible promoter or any other methods known in the art.

Optionally, at step 122, for PDMs generated from fixed samples (step 116), after a predetermined period of time (such as, 4-60 hours), cell growth medium is replaced with fresh media. In some embodiments, the replacement media is low serum media. Next, after an additional incubation period (such as, in the range of 4-24 hours), the PDMs are expressed under the control of a constitutive promoter.

Next, at step 124, after an additional period of time that allows for the expression of the PDMs in the test cells (such as, for example, in the range of about 4-48 hours), the subcellular localization of the FTR is determined Determination of the subcellular localization of the FTR may be performed by various means, such as, imaging using a fluorescent microscope, fractionation of subcellular compartments using biochemical methods, and the like. In some exemplary embodiments, the cells are fixed and the fluorescent FIR localization is determined by fluorescent imaging. Analysis and comparison of the subcellular localization of the FTR under various experimental conditions allows the determination as to whether the tested PDM is defective (i.e. mutated), or not. For example, subcellular localization of the FTR is determined in cells, in which it is co-expressed with the tested PDM (test assay). In addition, subcellular localization of the same FTR is determined in cells, in which it was co-expressed with WT PDM (control assay). Differences in subcellular localization of the FTR between the test assay and the control assay indicate as to the functional activity of the tested PDM. Thus, for example, in Step 126, if the FTR is identified in the test assay to be at the same subcellular localization as in the control assay, the tested PDM is not mutated. For example, in Step 128, if the FTR is identified in the test assay to be at the same subcellular localization as in the control assay, the tested PDM is mutated, which indicates that this PDM is a driver mutation.

Figure 2:
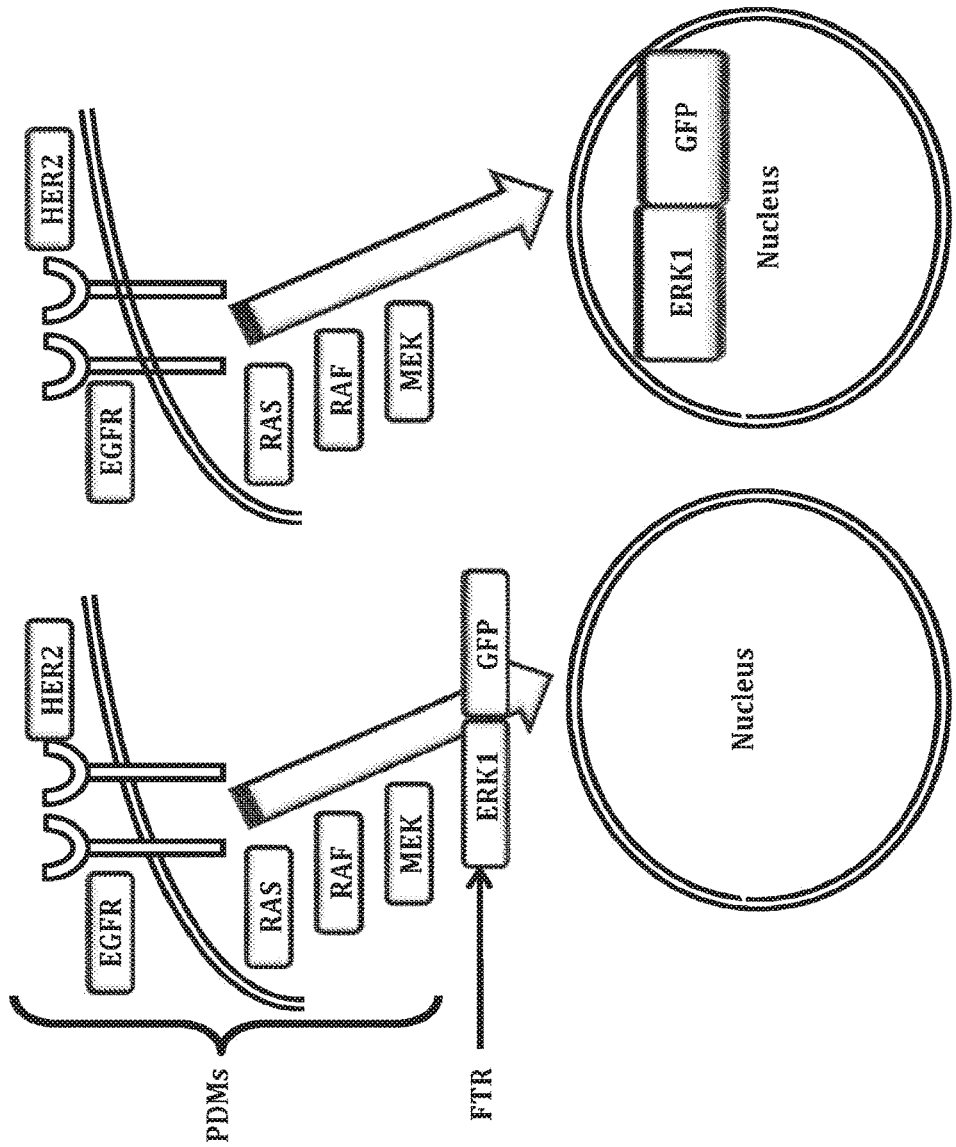
FIG. 2 is a schematic cartoon (not to scale) showing identification of specific patient driver mutations, according to some embodiments.

Reference is now made to FIG. 2, which is a schematic cartoon (not to scale) of application of the methods of the invention to identify driver mutations in an exemplary cell signaling pathway, according to some embodiments. As shown in FIG. 2, various PDMs which are members of the MAP kinase signaling pathway (EGFR, HER2, RAS, RAF, and MEK) are prepared from a biological sample of a patient, as described above. The FTR in this exemplary assay is a chimeric reporter comprising of a MAPK protein (ERK1 or ERIC) as the target (marker) gene portion, fused to a GFP reporter gene (as the reporter gene portion). Each of the PDMs and the FTR are processed as described above herein and the localization of the FTR under the various experimental conditions is determined As shown in the left hand panel (200), none of the tested PDMs is mutated, since the detected localization of the FTR is as in the WT condition (i.e. the FTR is localized to the cytoplasm)— therefore, none of the tested PDMs are mutated. As shown in the right hand panel (202), at least one of the tested PDMs is mutated, since the subcellular localization of the FTR is different than in the WT conditions (i.e., in this example, it is in the nucleus). Since each of the tested PDMs is individually tested with the FTR in a separate test cell, identification of the specific mutated PDM is achievable.

According to some embodiments, there is thus provided a method for identifying aberrant signal transduction pathways in biological samples of cancer patient, and/or for identifying one or more patient specific driver mutations, comprising one or more of the steps of (in any selected order):

a) obtaining a sample of plurality of mRNA from a biological sample of a cancer patient, such as from a biopsy of the tumor;

b) generating a cDNA library from the plurality of tumor mRNAs, by methods known in the art;

c) amplifying individual cDNA samples of the cDNA library using a set of primers complementary to polynucleotides (genes or gene portions) encoding for known proteins, wherein the proteins are involved in various cell signaling pathways;

d) forming individual expression constructs of the amplified cDNAs wherein the cDNAs are operably linked to a promoter, to produce test patient derived markers (test PDMs);

e) forming an addressable array of a first set of expression constructs harboring the amplified cDNAs from the tumor (test PDMs), and in parallel a second set of expression constructs of the corresponding (matching) wild type proteins (WT PDMs);

f) adding an expression vector for co-transfection of a marker gene linked to a specific reporter gene (FTR) for each locus in the array, wherein the marker gene is affected directly or indirectly by a corresponding PDM;

g) optionally drying the cDNA constructs on a support solid substrate;

h) adding viable assay cells to each locus under conditions enabling transfection of the DNA constructs into the assay cells;

i) allowing expression of the constructs and expression vector in the transfected cells to obtain gene products of the first set of cDNAs from the tumor and the specific reporter gene for each locus in the array;

j) comparing at least one attribute of the reporter gene in the cells expressing the cDNAs from the tumor with its corresponding wild type expressed cDNAs;

wherein a disparate result between the cells expressing tumor derived cDNA and the corresponding wild type cDNA is used for identifying the cDNA from the tumor sample as a candidate aberrant signal transduction protein.

In some embodiments, the expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In such embodiments, steps d) and f), above, are combined to one step: (alternative step d)): forming individual expression constructs of the amplified cDNAs wherein the cDNAs are operably linked to a promoter, to produce test patient derived markers (test PDMs); wherein said expression constructs further includes a specific reporter gene (FTR). In some embodiments, the FTR is linked to a promoter (that may be identical or different from the promoter of the PDM). In further embodiments, the FTR comprises a target gene portion linked to a reporter gene portion.

In some embodiments, step g) precedes steps e) and/or f), in which case the assay cells are added to each locus prior to addition of the expression cassettes.

According to some embodiments, there is thus provided a method of identifying one or more patient specific driver mutations in a biological sample of a cancer patient, comprising the steps of:

a) obtaining a plurality of mRNAs from the biological sample;

b) generating a cDNA library from the plurality of mRNAs;

c) amplifying specific cDNAs of the cDNA library using a set of primers complementary to polynucleotides encoding for known signal transduction proteins;

d) forming individual expression constructs of the amplified cDNAs wherein the cDNAs are operably linked to a promoter;

e) forming an addressable array of a first set of expression constructs harboring the amplified cDNAs from the tumor, and a second set of expression constructs of the corresponding wild type cDNAs;

thereby providing an addressable array of expression constructs harboring candidate mutations in polynucleotides encoding for the signal transduction proteins, the array is suitable for identifying patient specific driver mutations in a biological sample of the cancer patient.

In some embodiments, the method further comprises a step (f) of adding an expression vector encoding for a Fluorescence Translocation Reporter (FTR) gene comprising a target gene portion linked to a specific reporter gene portion for each locus in the array.

In further embodiments, the method further comprises the steps of: (g) adding viable assay cells to each locus under conditions enabling transfection of the DNA constructs and vectors into the assay cells; and (h) comparing at least one attribute of the expressed FTR in the assay cells expressing the cDNAs from the tumor with its corresponding wild type expressed cDNAs; wherein a disparate result between the assay cells expressing the cDNA derived from the biological sample of the cancer patient and the corresponding wild type cDNA, is used for identifying the cDNA from the biological sample as a candidate patient specific driver mutation.

According to some embodiments, there is provided a method of identifying one or more patient specific driver mutations in a biological sample of a cancer patient, comprising the steps of:

a) obtaining a plurality of mRNAs from the biological sample;

b) generating a cDNA library from the plurality of mRNAs;

c) amplifying specific cDNAs of the cDNA library using a set of primers complementary to polynucleotides encoding for known signal transduction proteins;

d) forming individual expression constructs of the amplified cDNAs wherein the cDNAs are operably linked to a promoter;

e) adding viable assay cells to a substrate, in an addressable array;

f) adding to the assay cells a first set of expression constructs harboring the amplified cDNAs from the tumor, and a second set of expression constructs of the corresponding wild type cDNAs; wherein each of the expression constructs is added to the assay cells at a disparate, addressable locus, under conditions enabling transfection of the expression constructs into the assay cells;

thereby generating an array of assay cells comprising expression constructs harboring candidate mutations in polynucleotides encoding for signal transduction proteins for identifying patient specific driver mutation in a biological sample of the cancer patient.

In some embodiments, the method further comprises a step of adding to the assay cells an expression vector of a Fluorescence Translocation Reporter (FTR) gene comprising a target gene portion linked to a specific reporter gene portion for each locus in the array.

In some embodiments, the method further comprises comparing at least one attribute of the FTR in the cells expressing the cDNAs from the tumor with its corresponding wild type expressed cDNAs; wherein a disparate result between the assay cells expressing the biological sample derived cDNA and the corresponding wild type cDNA is used for identifying the cDNA from the biological sample as a candidate patient specific driver mutation.

In some embodiments, the biological sample is selected from tumor cells, tumor biopsy, tumor tissue and bodily fluids.

According to some embodiments, there is provided a method for identifying aberrant signal transduction pathways in biological samples of cancer patient, and/or for identifying patient specific driver mutation, comprising one or more of the steps of (in any appropriate order):

a) obtaining a sample of a plurality of mRNAs from a biological sample of the cancer patient, such as from a biopsy of the tumor;

b) generating a cDNA library from the plurality of tumor mRNAs, by methods know in the art;

c) amplifying individual cDNA samples of the cDNA library using a set of primers complementary to polynucleotides encoding for known proteins, wherein the proteins are involved in various cell signaling pathways;

d) forming individual expression constructs of the amplified cDNAs wherein the cDNAs are operably linked to a promoter and to a reporter gene, to produce chimeric test patient derived reporters (test PDRs);

e) forming an addressable array of a first set of expression constructs harboring the amplified cDNAs from the tumor (test PDRs), and in parallel a second set of expression constructs of the cDNAs (wt PDRs);

f) optionally drying the cDNA constructs on a support solid substrate;

g) adding viable assay cells to each locus under conditions enabling transfection of the DNA constructs into the assay cells;

h) allowing expression of the constructs and expression vector in the transfected cells to obtain gene products of the first set of cDNAs from the tumor;

i) comparing at least one attribute of the chimeric reporter gene in the cells expressing the cDNAs from the tumor with its corresponding wild type expressed cDNAs;

wherein a disparate result between the cells expressing tumor derived cDNA and the corresponding wild type cDNA is used for identifying the cDNA from the tumor as a candidate aberrant signal transduction protein.

According to some embodiments, there is provided a method of identifying aberrant signal transduction pathways in tumor cells, comprising one or more of the steps of (in any appropriate order):

a) obtaining a sample of mRNA from tumor cells, that may be obtained in-vitro or in-vivo, for example, from a tumor biopsy;

b) generating a cDNA library from the plurality of mRNAs obtained;

c) amplifying individual cDNA samples of the cDNA library using a set of primers complementary to known signal transduction proteins;

d) forming individual expression constructs of the amplified cDNAs wherein the cDNAs are operably linked to a promoter;

e) forming an addressable array of a first set of expression constructs harboring the amplified cDNAs from the tumor, and in parallel a second set of expression constructs of the corresponding wild type cDNAs;

f) adding an expression vector for co-transfection of a Fluorescence Translocation Reporter (FTR) chimeric gene comprising a target gene portion linked to a reporter gene portion, for each locus in the array;

g) adding viable assay cells to each locus under conditions enabling transfection of the DNA constructs into the assay cells;

h) comparing at least one attribute of the expressed FTR in the cells expressing the cDNAs from the tumor with its corresponding wild type expressed cDNA;

wherein a disparate result between the cells expressing tumor derived cDNA and the corresponding wild type cDNA is used for identifying the cDNA from the tumor cells as a candidate aberrant signal transduction protein.

In some embodiments, the expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In some embodiments, step g) may precede steps e) and/or f), in which case the assay cells are added to each locus prior to addition of the expression constructs and/or expression vectors.

Accordingly, in accordance with some embodiments, there is provided a method for identifying aberrant signal transduction pathways in tumor cells, comprising one or more of the steps of (in any appropriate order):

a) obtaining a sample of mRNA from tumor cells, that may be obtained in-vitro or in-vivo, for example, from a tumor biopsy;

b) generating a cDNA library from the plurality of mRNAs obtained;

c) amplifying individual cDNA samples of the cDNA library using a set of primers complementary to polynucleotides encoding for known signal transduction proteins;

d) forming individual expression constructs of the amplified cDNAs wherein the cDNAs are operably linked to a first promoter; said expression constructs further comprise an expression cassette comprising a second promoter and encoding for a Fluorescence Translocation Reporter (FTR) chimeric gene, said FTR comprises a target gene portion linked to a reporter gene portion;

e) forming an addressable array of a first set of expression constructs harboring the amplified cDNAs from the tumor and the FTR cassette, and in parallel a second set of expression constructs of the corresponding wild type cDNAs and the FTR cassette;

f) adding viable assay cells to each locus under conditions enabling transfection of the DNA constructs into the assay cells; and g) comparing at least one attribute of the expressed FTR in the cells expressing the cDNAs from the tumor with its corresponding wild type expressed cDNA;

wherein a disparate result between the cells expressing tumor derived cDNA and the corresponding wild type cDNA is used for identifying the cDNA from the tumor cells as a candidate aberrant signal transduction protein.

In some embodiments, the first and second promoters are identical or different.

According to some embodiments, there is provided a method of identifying aberrant signal transduction pathways in tumor cells, comprising the steps of:

a) obtaining a plurality of mRNAs from the tumor cells;

b) generating a cDNA library from the plurality of mRNAs;

c) amplifying specific cDNAs of the cDNA library using a set of primers complementary to polynucleotides encoding for known signal transduction proteins;

d) forming individual expression constructs of the amplified cDNAs of step (c), wherein the cDNAs are operably linked to a promoter;

e) forming an addressable array of a first set of expression constructs harboring the amplified cDNAs from the tumor, and a second set of expression constructs of the corresponding wild type cDNAs;

thereby providing an addressable array of expression constructs harboring candidate mutations in the polynucleotides encoding for the signal transduction proteins, suitable for identifying aberrant signal transduction pathways in the tumor cells.

In some embodiments, the method further comprises a step (f) of adding an expression vector encoding for a Fluorescence Translocation Reporter (FTR) gene comprising a target gene portion linked to a reporter gene portion, for each locus in the array.

In additional embodiments, the method further comprises the steps of: g) adding viable assay cells to each locus under conditions enabling co-transfection of the DNA constructs into the assay cells; and h) comparing at least one attribute of the expressed FTR in the assay cells expressing the cDNAs from the tumor with its corresponding wild type expressed cDNAs; wherein a disparate result between the assay cells expressing cDNA derived from the tumor cells and the corresponding wild type cDNA is used for identifying the cDNA from the tumor cells as a candidate aberrant signal transduction protein.

According to some embodiments, a patient is a patient afflicted with cancer. In some embodiments, cancers include such cancers as: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, lung cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer is selected from prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer.

In some embodiments, the patient has been diagnosed positive for cancer. In some embodiments, the patient is subjected to targeted therapy treatment regimen with known or unknown treatment results. In some embodiments, the patient has an available patient tumor molecular profiling (IHC, FISH, PCR and sequencing). In some embodiments, the patient has available patient history as well as outcome (patient response, resistance, recurrence and survival rates).

In some embodiments, the biological sample is selected from: blood, scrum, biopsy, tissue, needle biopsy, bronchoalveolar lavage, pleural effusion urine, saliva and tumor. In some embodiments, the biological sample may be freshly isolated. In some embodiments, the biological sample may be frozen. In some embodiments, the biological sample may be fixed.

In some embodiments, each protein expressed in an assay cell (such as, tested PDM, FTR, WT PDM, PDR) is differentially identifiable. In another embodiment, each protein, directly or indirectly, may be identified by a different marker or reporter or a different fluorescent protein. In another embodiment, each chimeric protein (such as, FTR, or PDR) comprises a different reporter moiety. In another embodiment, different proteins may share a fluorescent protein or reporter. In another embodiment, each chimera protein of the invention comprises a different reporter moiety.

In another embodiment, a PDM is associated with cancer growth. In another embodiment, a PDM is an oncogene or tumor suppressor. In another embodiment, a PDM is a cytoskeletal regulator. In another embodiment, a PDM has a role in tumor growth and metastasis. In another embodiment, a PDM is a vesicle trafficking protein. In another embodiment, a PDM is a vesicle tethering protein. In another embodiment, a PDM is a cell adhesion protein. In another embodiment, a PDM is a nuclear integrity protein. In another embodiment, a PDM is a growth factor receptor. In another embodiment, a PDM is a cytokine receptor. In another embodiment, a PDM is a cell attachment protein. In another embodiment, a PDM is involved in tumor inflammation. In another embodiment, a PDM is a cell polarity protein. In another embodiment, a PDM is a signaling protein. In another embodiment, a PDM is an adaptor protein. In another embodiment, a PDM is a protein kinase.

In another embodiment, a PDM is an exchange factor. In another embodiment, a PDM is a cytoskeletal protein. In some exemplary embodiments, a PDM is selected from the group comprising or consisting of: AKT1, AKT2, AKT3, ALK, BRAF, BRCA1, BRCA2, CBL, CTNNB1, EGFR, ERBB2, ERBB3, FGFR1, FGFR2, GNA1 1, GNAQ, HRAS, JAK2, KIT, KRAS, MET, NRAS, PDGFRA, PIK3CA, PTEN, RAF1, RET, ROS1, SMO, TP53, SMAD2, SMAD3, SMAD4, STAT1, STAT3, STAT5B, TGFBR2, FBXW7, MYC, LKB1, SMARCA4, TCF7L2, MAP3K1, ESR1, AR, PR, DDR2, MEK1 or any combination thereof. Each possibility is a separate embodiment.

In another embodiment, a PDM is expressed in conjunction to marker (tag) such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1). In some embodiments, the marker comprises a marker a motif of Cys-Cys-Pro-Gly-Cys-Cys (SEQ ID NO:47), and prior to imaging to FIAsH-EDT2 or RcAsH-EDT2 may be added to the test assay, to become fluorescent upon binding to recombinant proteins containing the Cys-Cys-Pro-Gly-Cys-Cys motif. In some embodiments, the protein comprising the Cys-Cys-Pro-Gly-Cys-Cys may be the PDM, a fluorescent protein alone, or a fluorescent protein fused to a subcellular marker that can further be used to tag subcellular organelles, such as, for example, plasma membrane or nucleus. In some embodiments, the marker (tag) expressed in conjunction to the PDM is used as a marker to verify transfection and expression of the PDM is an assay cell.

In another embodiment, a PDR is a PDM fused to marker (tag) such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1. In some embodiments, a PDR is a PDM fused to marker (tag), comprising a Cys-Cys-Pro-Gly-Cys-Cys (SEQ ID NO:47) motif.

In some embodiments, the FIR is a fusion (chimeric) protein comprising a reporter portion, such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1) or a Cys-Cys-Pro-Gly-Cys-Cys motif, and a target protein portion selected from, but not limited to: a protein associated with cancer growth, an oncogene product, a cytoskeletal regulator, vesicle trafficking protein, vesicle tethering protein, cell adhesion protein, nuclear integrity protein, growth factor receptor, cell attachment protein, cell signaling protein, protein involved in tumor inflammation, cell polarity protein, growth factor signaling protein, an adaptor, a cytoskeletal protein, and the like. Each possibility is a separate embodiment.

In some exemplary embodiments, the FTR is a fusion protein comprising a reporter portion, such as a fluorescent protein, and a target (marker) protein portion selected from the group comprising or consisting of, but not limited to: AKT1, AKT2, mTOR, RelA, NFKB1, NFKB2, ERK1, ERK2, ERF, STAT1, STAT3, STAI5, CTNNB1, JNK1alpha, JNK1beta, JNK2alpha, JNK2beta, ERK5, P38alpha, P38beta, AMPK, STK11, SMARCA4, TP53, ESR1, GATA3, CDK2, SMAD1, NOTCHI, MYB, MYC, SMAD2, SMAD3, SMAD4, PRKACA, NLK or any combination thereof. Each possibility is a separate embodiment.

In some exemplary embodiments, the PDM may be KRas and the target portion of the FTR may be selected from: ERK2, ERF, JNK and AKT1. Each possibility is a separate embodiment.

In some exemplary embodiments, the PDM may be AKT2 or AKT3 and the target portion of the FTR may be selected from: AKT1 and RelA. Each possibility is a separate embodiment.

In some exemplary embodiments, the PDM may be FGFR1 and the target portion of the FTR may be selected from: ERK2, JNK (such as JNK1alpha 1), p38b, AKT1 and STAT3. Each possibility is a separate embodiment.

In some exemplary embodiments, the PDM may be BRaf and the target portion of the FTR may be selected from: ERK2 and ERF. Each possibility is a separate embodiment.

In some exemplary embodiments, the PDM may be EGFR and the target portion of the FTR may be selected from: ERK2, RelA, AKT1, p38b, JNK1a1. Each possibility is a separate 30 embodiment.

In another embodiment, the invention includes assay cells, wherein each assay cell expresses a PDM and/or an FTR. In another embodiment, the invention includes assay cells, wherein each assay cell expresses a different PDM and/or an FTR and/or PDR. In another embodiment, the invention includes assay cells, wherein each assay cell is transfected with a different DNA fragment, wherein each DNA fragment encodes a different PDM and/or an FTR. In some embodiments, the assay cells are placed/plated/grown on solid substrate having designated locuses (locations). In some embodiments, the assay cells are identical for each locus. In some embodiments, the assay cells are not identical for each locus. In some embodiments the assay cells are added in medium to each locus. In some embodiments, the cells are added to a solid substrate already having DNA constructs dehydrated thereto. In some embodiments, the cells are first plated on the solid substrate and transfected after a predetermined period of time.

In another embodiment, the invention includes assay cells, wherein each assay cell is transfected with a different DNA fragment, wherein each DNA fragment encodes a different 15 PDM and/or an FTR and/or PDR.

In some embodiments, identification of localization of the FTR is performed using a protein assay, binding assay, an immunoassay, microscopic imaging, or any other suitable assay known to those of skill in the art.

In some embodiments, the invention further includes the step of detecting a morphological change in an assay cell. In some embodiments, the methods of the invention do not require sequencing of any patient DNA.

According to some embodiments, there is provided a kit for diagnosing cancer in a patient. In some embodiments, there is provided a kit for identifying an aberrant cellular signaling pathway in tumor cells. In some embodiments, there is provided a kit for identifying patient specific driver mutations.

In some embodiments, the invention provides a kit for diagnosing cancer or the molecular cancer profile in a subject, by identifying patient specific driver mutations. The kit can be used, according to some embodiments, for predicting treatment success or identifying paracrine or autocrine factors involved in cancer. In another embodiment, the kit comprises at least one means of detecting a reporter gene. In another embodiment, the kit comprises means for detecting a marker. In some embodiments, the kit contains one or more of: a substrate or container for holding nucleic acid molecules and/or test cells, directions for carrying out detection/translocation assay(s), test cells, transfection reagents, or any combination thereof.

Diagnostic compositions of the present invention may, if desired, be presented in an article of manufacture e.g., kit, such as an FDA approved kit, which may contain diagnostic reagents and instructions for use. The kit may also be accommodated by a notice associated with the container in a form prescribed by a governmental agency regulating the manufacture, use or sale of pharmaceuticals, which notice is reflective of approval by the agency of the form of the compositions or human or veterinary use.

In another embodiment, the methods and kits of the invention increase survival of cancer patients. The assays of the present invention are ideally suited for the preparation of kits. Such a kit may comprise a carrier means being compartmentalized to receive in close confinement there with one or more container means such as vials, tubes, plates, slides, and the like, each of the container means comprising the separate elements of the cell assay.

In one embodiment, a kit for diagnosing cancer in a subject comprising a panel of assay cells each includes a different protein of the invention is provided, the kit comprising a substrate having nucleic acid molecules encoding for PDM (derived from a biological sample of the patient) and/or FTR and/or FTR, wherein the substrate is further capable of holding assay cells and a biological sample isolated from a human subject suspected of having cancer and printed instructions for reacting measuring and or detecting translocation events.

In some embodiments, transfected assay cells are cultured under effective conditions, which allow for the expression of recombinant protein or tagged proteins. In one embodiment, a tagged or marker protein of the invention (such as PDM, FTR) is a recombinant protein or a chimera. In some embodiments, effective culture conditions include, but are not limited to, effective media, bioreactor, temperature, $CO_2$, pH and oxygen conditions that permit protein expression. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, the present invention utilizes redistribution technology for monitoring and recording protein translocation event. In another embodiment, protein targets are labeled with the green fluorescent protein or other fluorescent proteins, and stably or transient transfected cell lines are generated. In another embodiment, the assays of the invention are read using a high-throughput, optical microscope-based instrument.

In another embodiment, protein translocation assay of the invention is high-content, high-throughput assay primarily used for profiling of lead series, primary screening of PDMs derived from biological samples as a constituent of cell media. In another embodiment, a protein translocation assay of the invention includes live-cell imaging, using Spinning Disc technology or any other microscopy based technology.

In some embodiments, a toponomic localization technique is used to follow and record protein translocation events. In some embodiments, means of immunofluorescence, of proteins of the invention, are utilized. In some embodiments, proteins of the invention are labeled with fluorescent markers. In some embodiments, confocal microscopic images are assessed and processed. In another embodiment, a standard dataset included 2-40 images of each cell per biological condition. In another embodiment, automated image analysis is performed. In another embodiment, automated image analysis includes cellular compartment or structure identification.

In another embodiment, spatial relations are captured in different dimensionalities. In another embodiment, quantitative assessment of protein-marker concentrations in bounded regions is performed. In another embodiment, the present invention further provides protein co-localization studies, based on measuring and evaluating isotropic distributions of distances between pixels. In another embodiment, the present invention provides a 2-dimensional analysis (regions). In another embodiment, the present invention further provides a 0-dimensional analysis (points). In another embodiment, the present invention provides 1-dimensional modeling.

The terms "comprises", "comprising", "includes", "including", "having" and their conjugates mean "including but not limited to". The terms "comprises" and "comprising" are limited in some embodiments to "consists" and "consisting", respectively. The term "consisting of means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "about" in reference to a numerical value stated herein is to be understood as the stated value+/−10%.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate some embodiments of the invention. They should, in no way be construed, however, as limiting the broad scope of the invention.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Biological Sample Collection

Both formalin fixed paraffin embedded (FFPE) tumor biopsies as well as frozen fresh tumor parts or biopsies are collected. The FFPE samples are used to extract specific genomic exons that are known to be involved in cancer progression (such as cKit exon 11). The fresh (fresh or fresh frozen) biopsy is used for both mRNA extraction and interstitial fluid extraction.

Thus, both retrospective and prospective samples are collected. Retrospective study based on frozen tumor sections from cases that the treatment efficacy is known.

Prospective study based on fresh or snap frozen sample/biopsy tissue/tumor section collected immediately following surgery/biopsy/bronchoscopy. This enables amplification of all relevant tested proteins (such as oncogenes or indicators). Other body fluids such as plasma samples (using Heparane sulfate gel tubes), blood samples, peritoneal fluid, pleural effusion and lung fluids obtained through bronchoscopy are of great importance as they accumulate much of the tumor secretions and are also collected.

Following tumor resection (surgery, biopsy, Bronchoscopy), the tumor tissue is placed in a sterile bag or tube on ice (not treated with formalin). A pathologist subdivides the tumor (taking into account size and location of viable tumor section) to those required for fixation and those best representing the tumor that are delivered fresh on ice for further analysis. The pathologist identifies a tissue section or area enriched with malignant cells and with reduced amount of stroma or other non-malignant tissue and excises it. If the net weight of the tissue exceeds 1 grams, tissue is further cut to several pieces and placed on a cellulose column and spun at 100 g for 10 min (100±50 microliter of IF are expected from every gram of tissue). Tissue is then transferred to another 15/50 ml tube and frozen in a −80° C. freeze. Spun down liquid known as the Interstitial fluid (IF) are frozen in original tube.

Needle biopsy—Tissue is placed in a 15 conical tube and frozen in a −80 freezer.

Biopsy via Bronchoscopy—Tissue is placed in a 15 conical tube and frozen in a −80 freezer.

Bronchoalveolar lavage—Extracted liquid is split between 2 50 ml falcon tubes and Spun down (3000 RPM, 15 min) Liquid is transferred into new tubes and both liquid and cells (in original tubes) are frozen at −80° C.

Pleural effusion—Pleural effusion is spun down (3000 RPM, 15 min.), liquid transferred into new tubes and both liquid and cells (in original tubes) frozen at −80° C.

Cryosection—if possible the tumor is frozen in a microtome and sectioned.

Extraction of Genomic DNA from Formalin Fixed Embedded Tumor Biopsies

To identify genes in which known mutations are present in specific exons, such as cKit mutations in exon 11, EGFR exons 19, 20, HER2 exon 20, DNA extracted from FFPE tissue is used. To this aim, standard DNA extraction kits and protocols are used (for example, Qiagen QIAamp DNA FFPE Tissue, cat. #56404).

Amplification of Exons and Insertion to Full Length Gene

To express desired exons, amplification from the genomic DNA is performed and insertion of the exon into the full length gene lacking this exon. To this aim, full length genes lacking the exon in expression ready vectors are produced and then the exon is incorporated into the construct using conventional molecular biology techniques.

Fresh Biopsies: Extraction of the Needed Amount of Tissue from Frozen Biopsy

A fraction of the biopsy is used for RNA purification and interstitial fluid extraction. The rest of biological material is stored for future reference or additional analysis (Immunohistochemistry (IHC), FISH, and the like).

Extraction of Interstitial Fluid (IF)

The interstitial fluid (IF) extracted as detailed below, is stored for later use as an agonist to the tested cells, to detect the presence of agents that are secreted by the tumor cells and may confer resistance to anti-cancer drugs.

IF extraction is performed by centrifuging the tissue sample in a column with glass fiber filter at 4° C. for 7 min at 1500 g. The fluids are then collected from the bottom part of the column into a new tube.

Extraction of mRNA mRNA extracted from the sample is needed for the amplification of the patient derived markers (PDMs), i.e. genes that are known oncogenes and potentially harbor mutations that provide the cell with oncogenic properties (genes with potential of harboring driver mutations). Exemplary genes that are tested include: AKT1, AKT2, AKT3, ALK, BRAF, BRCA1, BRCA2, CBL, CTNNB1, EGFR, ERBB2, ERBB3, FGFR1, FGFR2, GNA11, GNAQ, HRAS, JAK2, KIT, KRAS, MET, NRAS, PDGFRA, PIK3CA, PTEN, RAF1, RET, ROS1, SMO, TP53, SMAD2, SMAD3, SMAD4, STAT1, STAT3, STAT5B, TGFBR2, FBXW7, MYC, LKB1, SMARCA4, TCF7L2, MAP3K1, AR, PR, ESR1, DDR2, MEK1, and MEK2.

RNA extraction is performed by methods known in the art, including the Guanidium-Cesium Chloride Method, Guanidium Acid-Phenol Method and glass fiber filters that bind nucleic acids in the presence of chaotropic salts and/or by use of commercially available kits (such as Qiagen RNeasy kit cat #74106, in accordance with manufacturer instructions).

Generation of cDNA

To allow amplification of PDMs, cDNA is synthesized based on the mRNA extracted from the tissue. cDNA is synthesized based on the template mRNA using a RNA-dependent DNA polymerase reverse transcriptase enzyme and using oligo-dT primers, random hexameric primers, or specific primers. Exemplary protocol includes using Super-Script™ III First-Strand Synthesis SuperMix protocol (Life technologies, cat #18080-051).

Generation of Test PDMs

The generation of the test PDMs is performed in two steps: amplification of the selected PDMs and attachment of additional elements to allow their proper expression in the assay cells.

A preliminary PCR reaction containing the oligonucleotides related to the test PDMs that are amplified is performed, to allow over-representation of these selected genes within the cDNA sample.

In some examples, the cDNA sample is aliquoted into separate wells/tubes for each gene that is to be amplified.

Using primers designed for each PDM, a PCR reaction is performed to amplify the selected 10 PDM gene from the cDNA library.

The following sets of primers are used for the PCR amplification of the following tested PDMs (Table 1):

TABLE 1

| 3' primer | 5' primer | Accession number | PDM (name) |
| --- | --- | --- | --- |
| TCAGGCCGTGCCGCTGGC (SEQ ID NO: 2) | ATGAGCGACGTGGCTATTG T (SEQ ID NO: 1) | NM_ 001014431.1 | AKT1 (v-akt murine thymoma viral oncogene homolog 1) |
| TCACTCGCGGATGCTGG (SEQ ID NO: 24) | ATGAATGAGGTGTCTGTCA TCAAAG (SEQ ID NO: 23) | NM_001626.4 | AKT2 (v-akt murine thymoma viral oncogene homolog 2) |
| TTATTCTCGTCCACTTGCA GAG (SEQ ID NO: 26) | ATGAGCGATGTTACCATTG TG (SEQ ID NO: 25) | NM_005465.4 | AKT3 (v-akt murine thymoma viral oncogene homolog 3) |

TABLE 1-continued

| 3' primer | 5' primer | Accession number | PDM (name) |
|---|---|---|---|
| TCAGTGGACAGGAAACGC AC (SEQ ID NO: 4) | ATGGCGGCGCTGAGCGGTG ((SEQ ID NO: 3) | N_004333.4 | BRAF (v-raf murine sarcoma viral oncogene homolog B) |
| TCATGCTCCAATAAATTCA CTGCT (SEQ ID NO: 6) | ATGCGACCCTCCGGGACG (SEQ ID NO: 5) | NM_005228.3 | EGFR (Epidermal growth factor) |
| TCAGGAGAGCACACACTT GC (SEQ ID NO: 8) | ATGACGGAATATAAGCTGG TGGT (SEQ ID NO: 7) | NM_005343.2 | HRAS (Harvey rat sarcoma viral oncogene homolog) |
| TTAGACGCCAGCAGCATG G (SEQ ID NO: 10) | ATGCCCAAGAAGAAGCCG AC (SEQ ID NO: 9) | NM_002755.3 | MEK1 (mitogen-activated protein kinase kinase 1) |
| TTACATCACCACACATGGC A (SEQ ID NO: 12) | ATGACTGAGTACAAACTGG TGGT (SEQ ID NO: 11) | NM_002524.4 | NRAS (neuroblastoma RAS viral (v-ras) oncogene homolog) |
| TTACAGGAAGCTGTCTTCC ACC (SEQ ID NO: 14) | ATGGGGACTTCCCATCCGG (SEQ ID NO: 13) | NM_006206.4 | PDGFRA (platelet-derived growth factor receptor, alpha polypeptide) |
| TCAGTTCAATGCATGCTGT T (SEQ ID NO: 16) | ATGCCTCCACGACCATCAT C (SEQ ID NO: 15) | NM_006218.2 | PIK3CA (phosphatidylino sitol-4,5-bisphosphate 3-kinase, catalytic subunit alpha) |
| TCAGACTTTTGTAATTTGT GTATGC (SEQ ID NO: 18) | ATGACAGCCATCATCAAAG AGA (SEQ ID NO: 17) | NM_000314 | PTEN (phosphatase and tensin homolog) |
| CTAGAAGACAGGCAGCCT CG (SEQ ID NO: 20) | ATGGAGCACATACAGGGA GC (SEQ ID NO: 19) | NM_002880.3 | RAF1 (v-raf-1 murine leukemia viral oncogene homolog 1) |
| TCAGTCTGAGTCAGGCCCT T (SEQ ID NO: 22) | ATGGAGGAGCCGCAGTCA (SEQ ID NO: 21) | NM_000546.5 | TP53 (tumor protein p53) |
| TCAGCGGCGTTTGAGTC (SEQ ID NO: 28) | ATGTGGAGCTGGAAGTGC (SEQ ID NO: 27) | NM_023110.2 | FGFR1 (Fibroblast growth factor 1) |
| TCATGTTTTAACACTGCCG TTTATG (SEQ ID NO: 30) | ATGGTCAGCTGGGGTCG (SEQ ID NO: 29) | NM_000141.4 | FGFR1 (Fibroblast growth factor 2) |
| TTACATAATTACACACTTT GTCTTTGACTTC (SEQ ID NO: 32) | GCCTGCTGAAAATGACTGA ATATAAAC (SEQ ID NO: 31) | NM_004985.3 | KRAS (Kirsten rat sarcoma viral oncogene homolog) |
| TTATGACATGCTTGAGCAA CG (SEQ ID NO: 34) | ATGTCGTCCATCTTGCCAT TC (SEQ ID NO: 33) | NM_005901.5 | SMAD2 (SMAD family member 2) |

Once the PDM gene regions are amplified, a second PCR reaction is performed to add to the 5' end of each PDM gene sequence, a promoter (either constitutive promoter such as CMV or an inducible promoter such as tetracycline promoter) and to the 3' end an IRES followed by a fluorescent reporter gene (such as GFP, RFP, BFP, or any other reporter gene, as designated).

In some examples, the addition of the promoter and IRES+fluorescent reporter elements is performed by molecular biology cloning tools, by fusing the PCR products to the desired elements by PCR approaches, ligation enzymes or recombination approaches (such as T4 DNA ligase or InFusion enzymes (Clontech), respectively).

When the full length nucleic acid molecule is formed (i.e. 5' promoter-PDM-3'IRES+Reporter (or any other order of these elements)), amplification using a PCR reaction is performed, to obtain sufficient amount of the nucleic acid molecule for transfection into cells.

In some cases, amplification of the nucleic acid molecule is achieved by ligating the full length nucleic acid molecule into an appropriate expression vector and transformation into bacteria. Plasmids thus formed are extracted using standard plasmid extraction kits such as Qiagen QIAprep Miniprep kit. In some case, the linear PCR fragments of the various PDMs are used for transfection into test cells.

Generation of FTRs:

The following sets of primers were used for the PCR amplification of the target portions of the following FTRs (Table 2):

In one option, the transfection mixes are placed and optionally dehydrated on an appropriate solid support substrate. In various settings, the substrate includes various solid substrates, such as: microscope slides, chip, cell culture plates, multi-plate wells, 96-well plates, 384-well plates and the like. Each mixture is placed in a designated, traceable locus/spot (i.e. a designated well or a designated location on the slide or chip). To the transfection mixtures on the substrate, a fixed number of cells (in the range of about 100 to 100,000, depending on the substrate type and as described above) is dispensed onto each spot, in normal full growth media. The cells are selected from HeLa cells, HEK 293 cells, NCI60 cell lines such as A549, EKVX, T47D, HT29 or any other suitable cell line, based on the tested PDM and assay. The test cells are placed on the solid substrate and incubated for 12-48 hours, in accordance with the type of cell, growth media and transfection conditions. The incubation time allows the cells to adhere to the substrate, and to introduce and express the FTR and PDM.

In another option, cells are plated on the solid substrate according to a predesigned matrix (in a designated, traceable locus/spot (i.e. a designated well or a designated location on the slide or chip)). After a predetermined period of time, the cells are transfected with the FTR and the appropriate PDM (WT PDM or test PDM), under appropriate transfection conditions. The FTR and the appropriate PDM may be located on two separate molecules, or on a single molecule encoding for both genes.

TABLE 2

| 3' primer | 5' primer | Accession number | FTR (name) |
| --- | --- | --- | --- |
| TCAGGCCGTGCCGCT GGC (SEQ ID NO: 2) | ATGAGCGACGTGGC TATTGT (SEQ ID NO: 1) | NM_001014431.1 | AKT1 (v-akt murine thymoma viral oncogene homolog 1) |
| TTAAGATCTGTATCCT GG (SEQ ID NO: 36) | ATGGCGGCGGCGGC GG (SEQ ID NO: 35) | NM_002745.4 | ERK2 (mitogen-activated protein kinase 1) |
| TCAGGAGTCTCGGTG CTCC (SEQ ID NO: 38) | ATGAAGACCCCGGC GGACAC (SEQ ID NO: 37) | NM_0064942 | ERF (Ets2 repressor factor) |
| TCACTGCTGCACCTG TGC (SEQ ID NO: 40) | ATGAGCAGAAGCAA GCG (SEQ ID NO: 39) | NM_002750.3 | JNK1a1 (mitogen-activated protein kinase 8 alpha 1) |
| TAGGAGCTGATCTGA CTCAGC (SEQ ID NO: 42) | ATGGACGAACTGTT CCCCCT (SEQ ID NO: 41) | NM_021975.3 | RelA (v-rel avian reticuloendotheliosis viral oncogene homolog A) |
| TCACTGCTCAATCTCC AGGC (SEQ ID NO: 44) | ATGTCGGGCCCTCG (SEQ ID NO: 43) | NM_002751.5 | P38b (mitogen-activated protein kinase 11) |
| TCACATGGGGGAGGT AGC (SEQ ID NO: 46) | ATGGCCCAATGGAA TCAG (SEQ ID NO: 45) | NM_139276.2 | STAT3 (signal transducer and activator of transcription 3) |

Transfection of Expression Constructs (FTR and PDM Mixtures)

According to a predesigned matrix, each reporter gene (FIR) that is used in the analysis is mixed with either a control wild type PDM gene or a test PDM gene, prepared as described above, and mixed with appropriate transfection reagents.

Assay Implementation: Inducible Promoter

Following adequate expression of the reporter FTR, growth media is replaced with low 25 serum media (to remove any growth factors/ligands present in the media), to reduce to minimum background stimulated signaling.

When signaling level is significantly reduced (within 4 to 16 hours), induction of PDM expression is initiated. This is achieved by addition of tetracyclin when using a tetracyclin inducible promoter and ecdysone when using an ecdysone inducible promoter.

In some examples, interstitial fluid (IF) and/or anti-cancer drugs are added to induce expression of the PDM, to thereby test the effect of the IF or drug on the PPM.

Assay Implementation—Constitutive Promoter

Following adequate expression of FTR and PDM in the cells (both under the control of a constitutive promoter), growth media is replaced with low serum media (to remove of any growth factors/ligands present in the media) to reduce to minimum background stimulated signaling.

In some examples, interstitial fluid and/or anti-cancer drugs are added to induce expression of the PDM, and thereby test the effect of the IF or drug on the PDM.

Image Acquisition and Analysis

Following PDM expression (30 hours after transfection), cells are fixed by washing 3 times with phosphate buffered saline (PBS), incubation for 5 minutes in 4% paraformaldehyde (PFA), and 3 subsequent washes with PBS. The slide is then covered by a cover slip and the localization of each corresponding FTR is imaged.

Image analysis of each FTR, both in control wild-type cells as well as in the PDM transfected cell, is performed and comparison is made. The difference between the localization of the FTR in control cells vs. PDM transfected cells, is quantified, and used to determine whether an oncogenic or a wild type form of the tested PDM was present in the tested sample. The quantification is done using standard image analysis software, such as ImageJ.

An exemplary assay using HeLa cells as the assay cells:

Day 0: slides are precoated with poly-1-lysine 0.01%, for 5 minutes at room temperature (RT) and then washed with sterile water (DDW). The water is aspirated and the slides are dried for 2 hrs. HeLa cells are plated (15000 cells) in 200µ complete medium for each well (complete medium: DMEM, 10% FBS, 1% pen/strep (P/S)).

Day 1: Transfection reagent (FugeneHD reagent (Promege, Cat. NO. E2311) is warmed to RT and Vortexed. For each well, a transfection mix is prepared in tubes, which includes: 50/100/200 ng expression construct of the PDM in tubes; 50/100 ng of expression construct of the appropriate FTR; Optimem buffer (to a total of 10µ) and FugeneHD (10 µl for each 3 µg of DNA). The transfection mixture is incubated at RT for 15 minutes.

The cell medium is aspirated from the wells, and each well is supplemented with 100 µl transfection medium (DMEM, 10% FCS, no antibiotics). 10 µl of the transfection mixture is added to each well. The cells are then incubated at 37° C. in humidified incubator (5% $CO_2$).

Six-eight hours later, the medium is replaced to starvation medium 1 (DMEM with 0.1% FCS, 1% Pen/Strep) and the cells are incubated at 37° C. humidified incubator, 5% $CO_2$.

Day 2: 26 hours later (i.e., 4 hours prior to fixation of the cells), the medium is changed to starvation medium 2 (DMEM with 0.1% FCS, 1% P/S). The cells are then incubated at 37° C. in humidified incubator (5% $CO_2$).

Figure 6A:
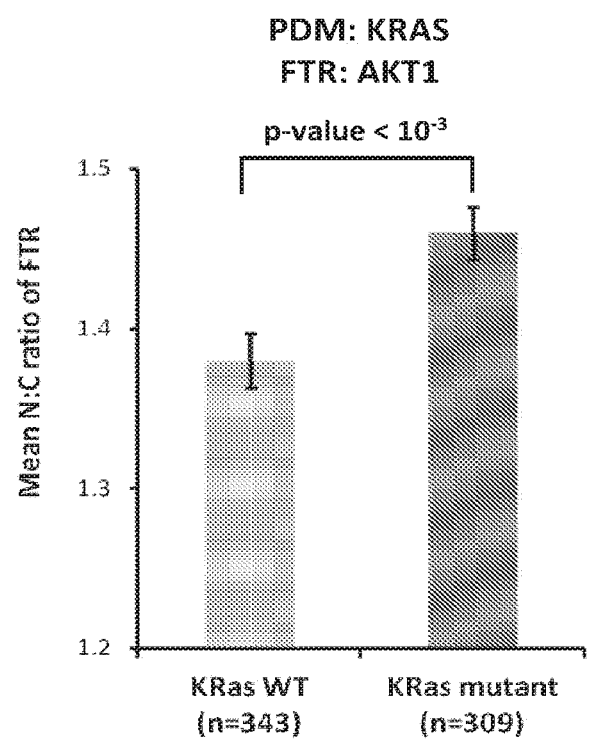
FIG. 6A—A bar graph showing results of a cell based assay in which the genes encoding KRas in wild type (KRAS WT) or mutant form (KRAS mutant (G13D)) have been expressed in test cells, along with a reporter protein (FTR), and the amount of the FTR (AKT1-GFP) in the cytoplasm and in the nucleus was quantified, based on fluorescence microscope images of the cells (fixed 30 hours after transfection). The ratio between the intensity of the FTR (AKT1) in the nucleus (N) and cytoplasm (C) was measured (N:C ratio). The number of cells measured (n) is indicated for each condition.
Figure 6B:
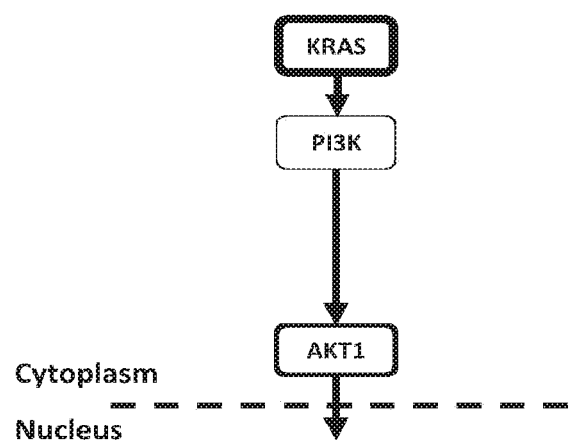

For assays which require inducement of signaling: Replace medium with starvation medium 2 supplemented with 20 ng/ml EGF, 5 min The cells are then incubated at 37° C. in humidified incubator (5% $CO_2$). This was done in Example 1 (FIG. 6) and example 2 (FIGS. 9-10).

30 hours after transfection, the cells are fixed (all steps at room temp) by the following process: the cells are washed 3 times with PBS, Fixed with fixation solution (5% Glucose/ 4% paraformaldehyde (PFA) in PBS) for 10 minutes, Washed 3 times with PBS. The cells are optionally stained with DAPI solution, after which they are washed three times with PBS.

Figure 3A:
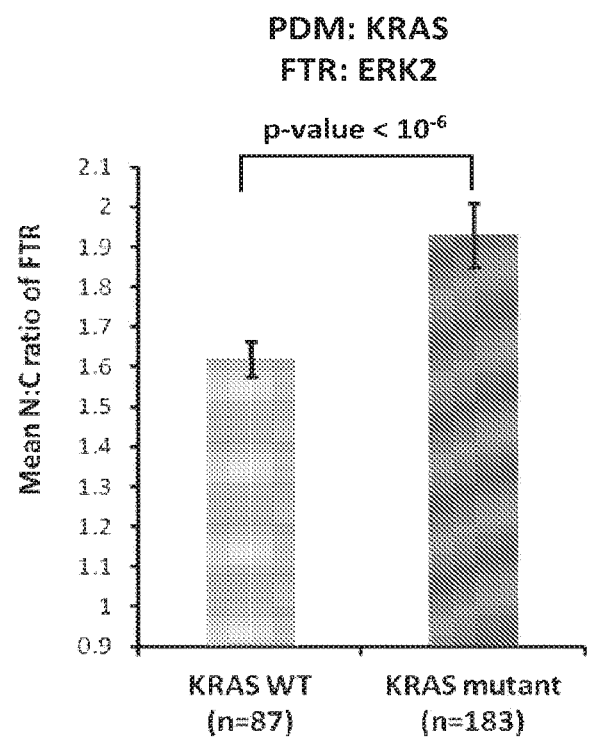
FIG. 3A—A bar graph showing results of a cell based assay in which the genes encoding KRas in wild type (KRAS WT) or mutant form (KRAS mutant (G13D)) have been expressed in test cells, along with a reporter protein (FTR), and the amount of the FIR (ERK2-GFP) in the cytoplasm and in the nucleus was quantified, based on fluorescence microscope images of the cells (fixed 30 hours after transfection). The ratio between the intensity of the FTR (ERK2) in the nucleus (N) and cytoplasm (C) was measured (N:C ratio). The number of cells measured (n) is indicated for each condition.
Figure 3B:
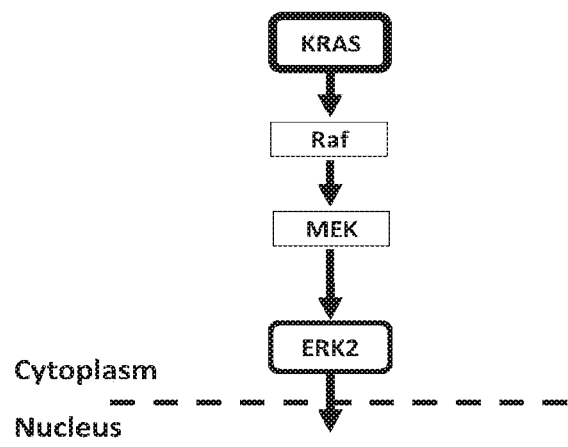
Figure 4A:
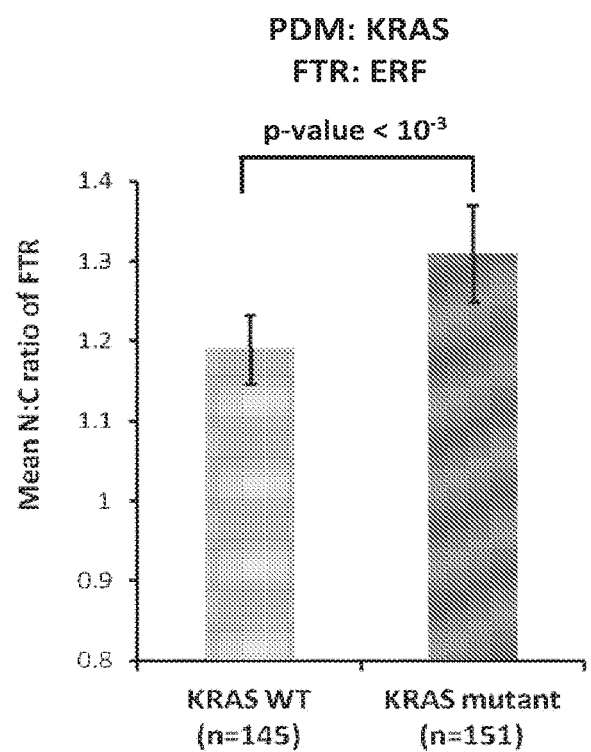
FIG. 4A—A bar graph showing results of a cell based assay in which the genes encoding KRas in wild type (KRAS WT) or mutant form (KRAS mutant (G13D)) have been expressed in test cells, along with a reporter protein (FTR), and the amount of the FTR (ERF-GFP) in the cytoplasm and in the nucleus was quantified, based on fluorescence microscope images of the cells (fixed 30 hours after transfection). The ratio between the intensity of the FTR (ERF) in the nucleus (N) and cytoplasm (C) was measured (N:C ratio). The number of cells measured (n) is indicated for each condition.
Figure 4B:
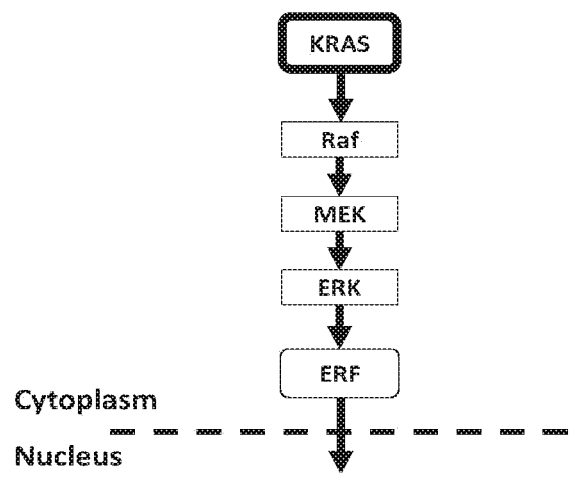
Figure 5A:
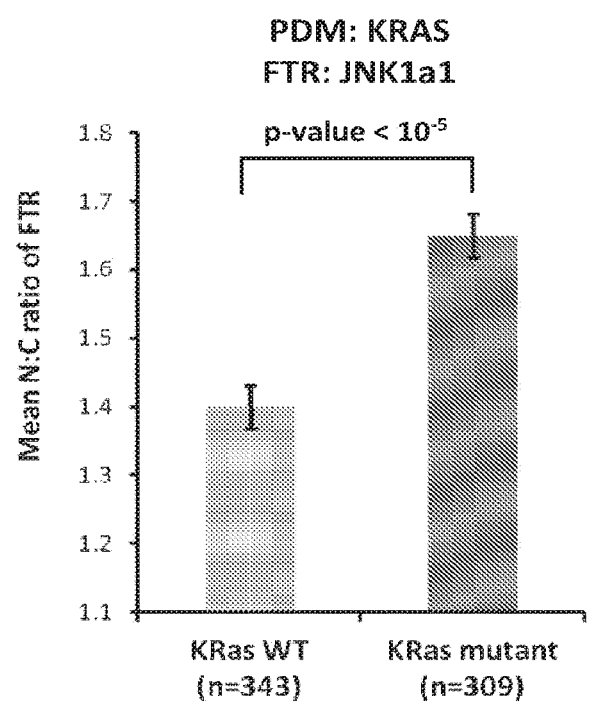
FIG. 5A—A bar graph showing results of a cell based assay in which the genes encoding KRas in wild type (KRAS WT) or mutant form (KRAS mutant (G13D)) have been expressed in test cells, along with a reporter protein (FTR), and the amount of the FTR (JNK1a1-GFP) in the cytoplasm and in the nucleus was quantified, based on fluorescence microscope images of the cells (fixed 30 hours after transfection). The ratio between the intensity of the FTR (JNK1a1) in the nucleus (N) and cytoplasm (C) was measured (N:C ratio). The number of cells measured (n) is indicated for each condition.
Figure 5B:
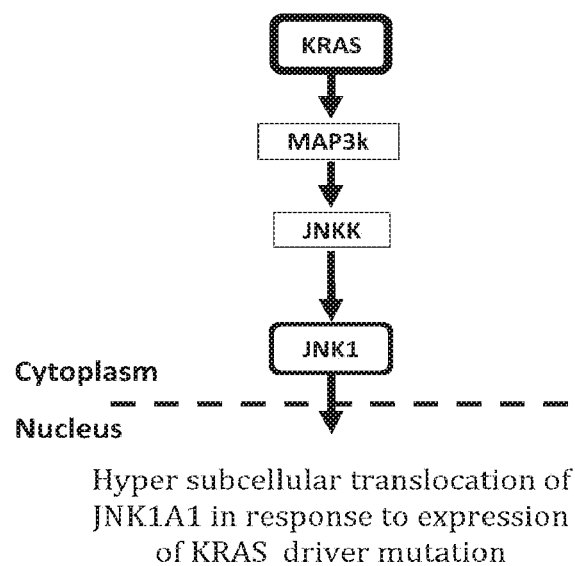

Example 1: Subcellular Translocation Assay of the ERK1/2, JNK and AKT Pathways can Discriminate Between the WT and Mutant KRas and Identify KRas Driver Mutations HeLa assay cells were transfected (as detailed above), with the indicated WT and mutated PDM (KRAS-WT and mutated KRAS harboring a known driver mutation (G13D)), along with a corresponding FTR. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIG. 3A-FIG. 6A. In FIG. 3A, the FTR is ERK2, in FIG. 4A, the FTR is ERF, in FIG. 5A, the FTR is JNK1alpha1, and in FIG. 6A, the FTR is AKT1. FIGS. 3B-6B schematically show the oncogenic map of the signaling pathway affected by the PDM (KRAS) as determined by the localization of the respective FTR. Altogether, the results show that the tested KRAS harboring the G13D mutation activates 3 different signaling pathways: ERK1/2, JNK and AKT.

Figure 7A:
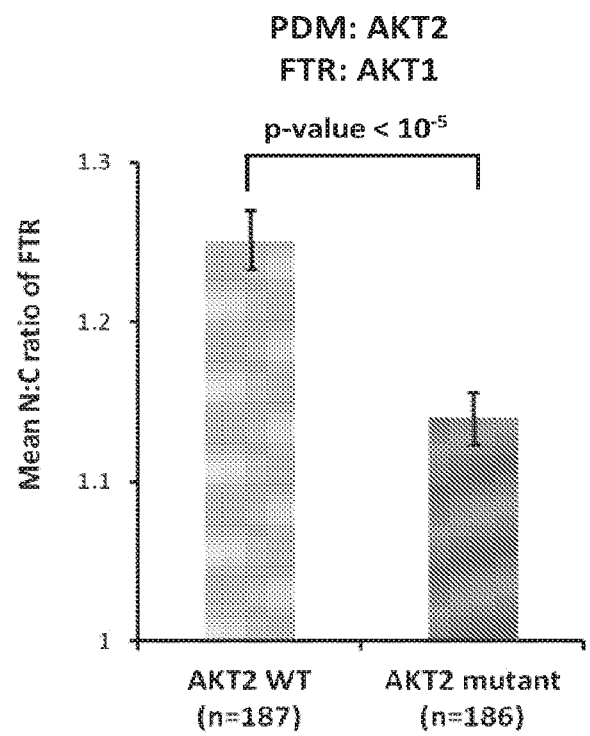
FIG. 7A—A bar graph showing results of a cell based assay in which the genes encoding AKT2 in wild type (AKT2 WT) or mutant form (AKT2 mutant (R251W)) have been expressed in test cells, along with a reporter protein (FTR), and the amount of the FTR (AKT1-GFP) in the cytoplasm and in the nucleus was quantified, based on fluorescence microscope images of the cells (fixed 30 hours after transfection). The ratio between the intensity of the FTR (AKT1) in the nucleus (N) and cytoplasm (C) was measured (N:C ratio). The number of cells measured (n) is indicated for each condition.
Figure 7B:
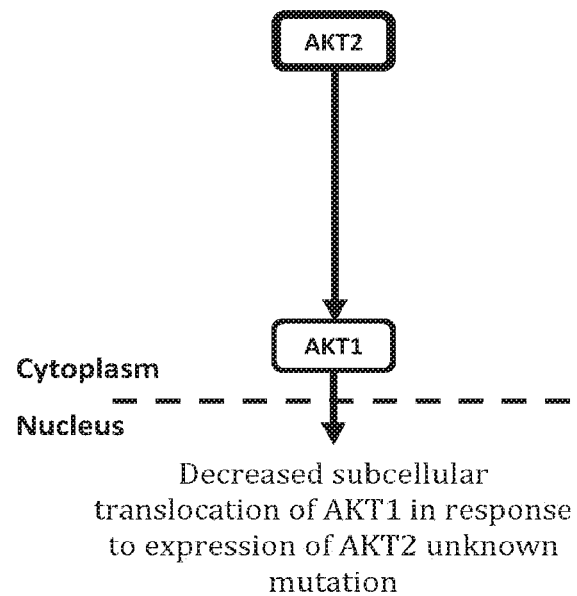
Figure 8A:
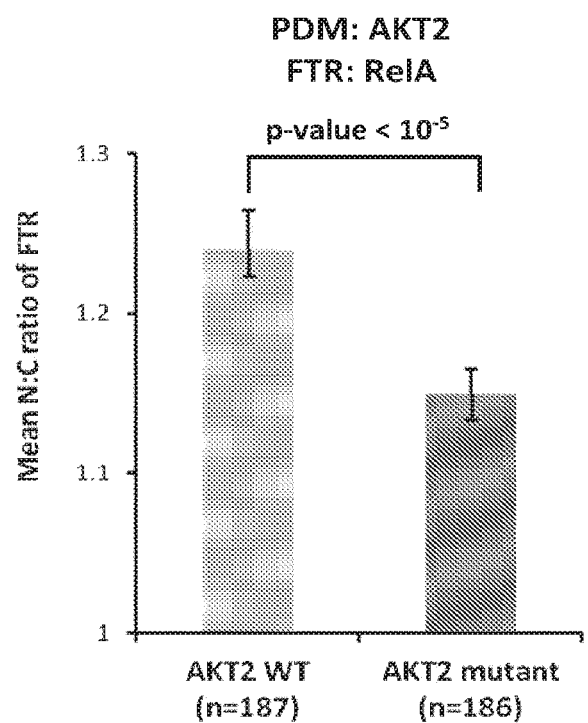
FIG. 8A—A bar graph showing results of a cell based assay in which the genes encoding AKT2 in wild type (AKT2 WT) or mutant form (AKT2 mutant (R251W)) have been expressed in test cells, along with a reporter protein (FTR), and the amount of the FTR (RelA-GFP) in the cytoplasm and in the nucleus was quantified, based on fluorescence microscope images of the cells (fixed 30 hours after transfection). The ratio between the intensity of the FTR (RelA) in the nucleus (N) and cytoplasm (C) was measured (N:C ratio). The number of cells measured (n) is indicated for each condition.
Figure 8B:
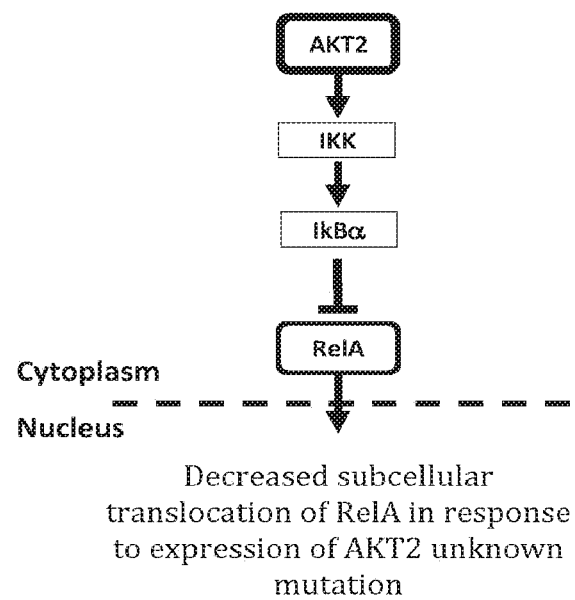

Example 2: Subcellular Translocation Assay of the AKT and NFkB Pathways can Discriminate Between the WT and Mutant AKT2 and Identify AKT2 Driver Mutations HeLa assay cells were transfected (as detailed above), with the indicated WT and mutated PDM (AKT2-WT and mutated AKT2 harboring functionally unknown mutation (R251W), that reside in the kinase domain of AKT2, in close proximity to an inhibitor binding site), along with a corresponding FTR. 30 hours after transfection, cells were fixed and imaged utilizing a fluorescence microscope. The amount of the FTR in the cytoplasm and in the nucleus was quantified. The ratio between the intensity of the FIR in the nucleus (N) and cytoplasm (C) was measured (N:C ratio). The results are presented in FIGS. 7A and 8A. In FIG. 7A, the FTR is AKT1, in FIG. 8A, the FTR is RelA. FIGS. 7B-8B schematically show the oncogenic map of the signaling pathway affected by the PDM (AKT2) as determined by the localization of the respective FTR. Altogether, the results show that the tested AKT2 harboring a R251W mutation affects the two different signaling pathways tested (AKT and NFkB), by decreasing the nuclear translocation of the tested FTRs.

Figure 9A:
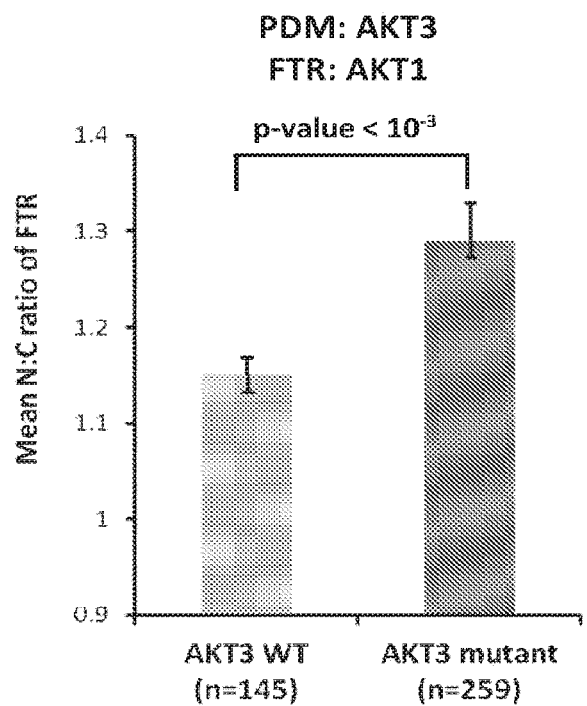
FIG. 9A—A bar graph showing results of a cell based assay in which the genes encoding AKT3 in wild type (AKT3 WT) or mutant form (AKT3 mutant (R465Q)) have been expressed in test cells, along with a reporter protein (FTR), and the amount of the FTR (AKT1-GFP) in the cytoplasm and in the nucleus was quantified, based on fluorescence microscope images of the cells (fixed 30 hours after transfection). The ratio between the intensity of the FTR (AKT1) in the nucleus (N) and cytoplasm (C) was measured (N:C ratio). The number of cells measured (n) is indicated for each condition.
Figure 9B:
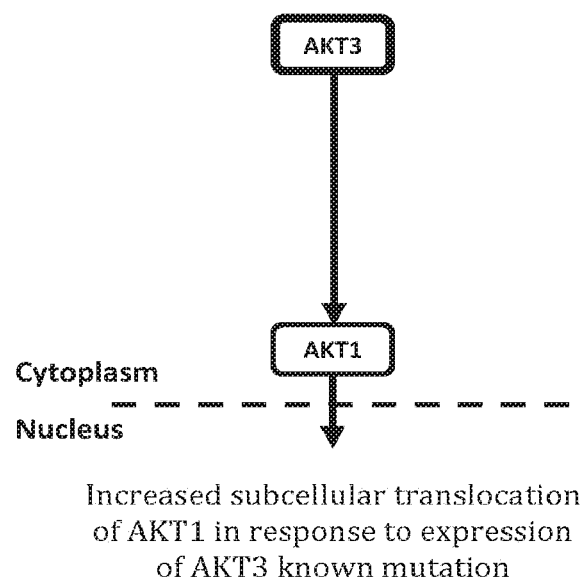
Figure 10A:
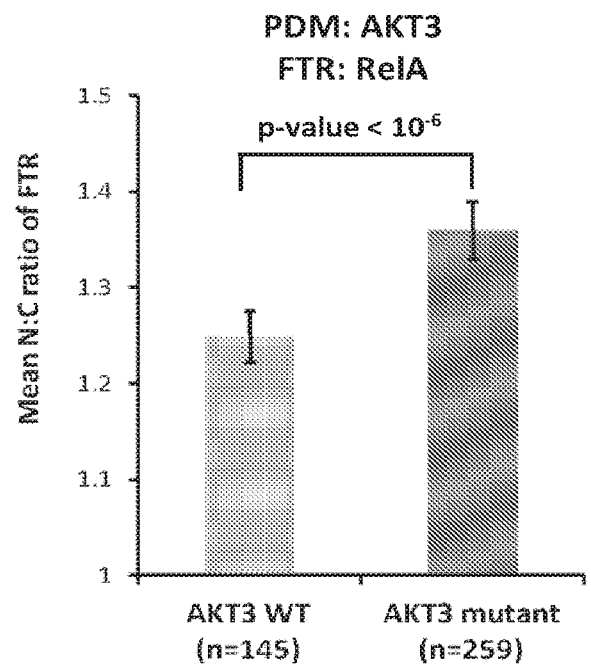
FIG. 10A—A bar graph showing results of a cell based assay in which the genes encoding AKT3 in wild type (AKT3 WT) or mutant form (AKT3 mutant (R465Q)) have been expressed in test cells, along with a reporter protein (FTR), and the amount of the FTR (RelA-GFP) in the cytoplasm and in the nucleus was quantified, based on fluorescence microscope images of the cells (fixed 30 hours after transfection). The ratio between the intensity of the FTR (RelA) in the nucleus (N) and cytoplasm (C) was measured (N:C ratio). The number of cells measured (n) is indicated for each condition.
Figure 10B:
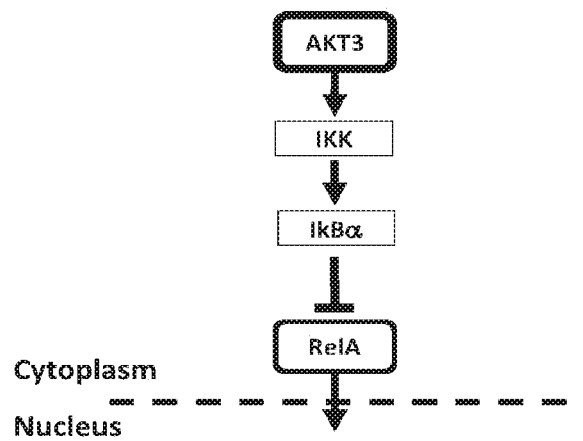

Example 3: Subcellular Translocation Assay of the AKT and NFkB Pathways can Discriminate Between the WT and Mutant AKT3 and Identify AKT3 Driver Mutations HeLa assay cells were transfected (as detailed above), with the indicated WT and mutated PDM (AKT3-WT and mutated AKT3 harboring an activating mutation (R465Q), reported to be involved in syndromes of sporadic overgrowth disorders associated with markedly enlarged brain size), along with a corresponding FTR. The inducible promoter of the tested PDMs was induced as described above. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 9A and 10A. In FIG. 9A, the FTR is AKT1, in FIG. 10A, the FTR is RelA. FIGS. 9B-10B schematically show the oncogenic map of the signaling pathway affected by the PDM (AKT3) as determined by the localization of the respective FTR. Altogether, the results show that the tested AKT3 harboring a R564Q mutation affects the two different signaling pathways tested (AKT and NFkB), by increasing the nuclear translocation of the tested FTRs.

Figure 11A:
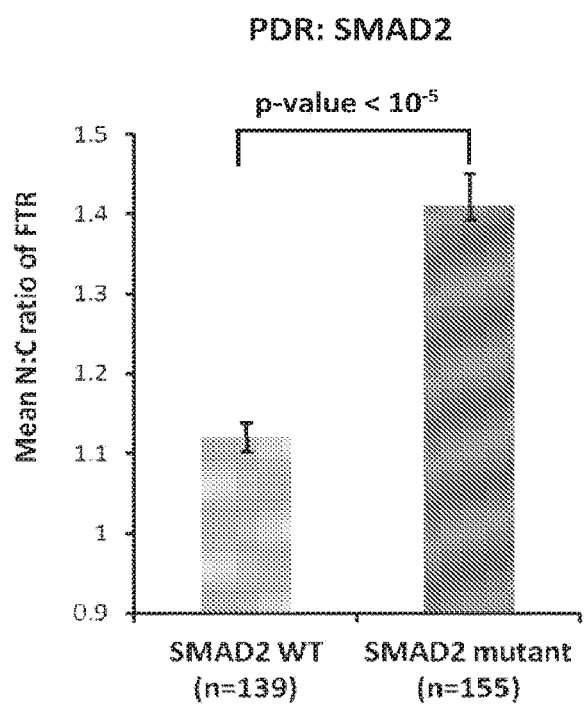
FIG. 11A—A bar graph showing results of a cell based assay in which the genes encoding SMAD2 in wild type (SMAD2 WT) or mutant form (SMAD2 mutant (T67A)) have been expressed in test cells, and the amount of the SMAD2 protein, serving as a patient derived reporter (PDR) protein in the cytoplasm and in the nucleus was quantified, based on fluorescence microscope images of the cells (fixed 30 hours after transfection). The ratio between the intensity of the protein in the nucleus (N) and cytoplasm (C) was measured (N:C ratio). The number of cells measured (n) is indicated for each condition.
Figure 11B:
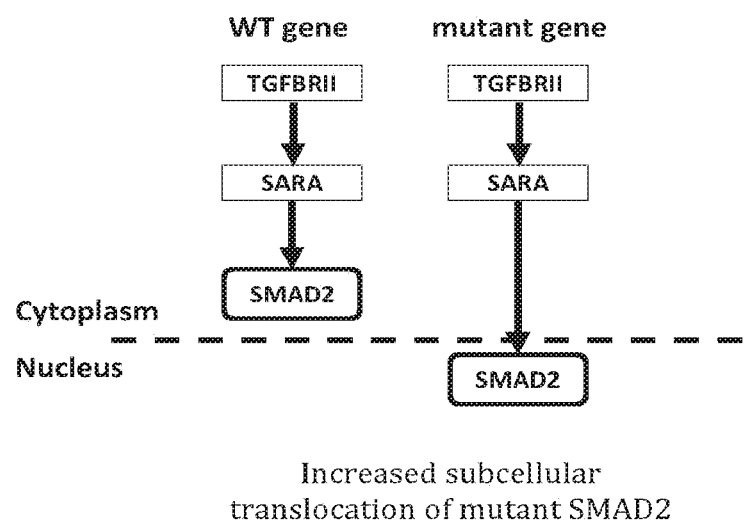

Example 4: Subcellular Translocation Assay of the SMAD2 Pathway can Discriminate Between the WT and Mutant SMAD2 and Identify SMAD2 Driver Mutations HeLa assay cells were transfected (as detailed above), with the indicated WT and mutated PDR (SMAD3-WT and mutated SMAD3 harboring an unknown mutation (T67A), which resides in the MH1 domain that interacts with other transcription factors). SMAD2 mediates the signal of TGF-beta, and thus regulates multiple cellular processes, such as cell proliferation, apoptosis, and differentiation. 30 hours after transfection, cells were fixed and imaged utilizing a fluorescence microscope. The amount of the PDR (SMAD2) in the cytoplasm and in the nucleus was quantified. The ratio between the intensity of the WT SMAD2 and mutated SMAD2 in the nucleus (N) and cytoplasm (C) was measured (N:C ratio). The results are presented in FIGS. 11A-B. As shown, the T67A mutation in SMAD2 causes SMAD2 to translocate into the nucleus, without any other induced stimulation of the cells.

Figure 12A:
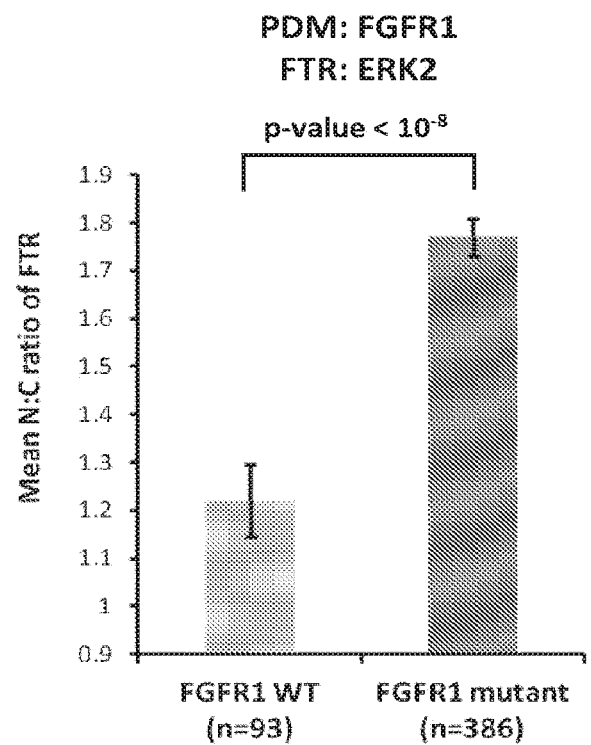
FIG. 12A—A bar graph showing results of a cell based assay in which the genes encoding FGFR1 in wild type (FGFR1 WT) or mutant form (FGFR1 mutant (A343V)) have been expressed in test cells, along with a reporter protein (FTR), and the amount of the FTR (ERK2-GFP) in the cytoplasm and in the nucleus was quantified, based on fluorescence microscope images of the cells (fixed 30 hours after transfection). The ratio between the intensity of the FTR (ERK2) in the nucleus (N) and cytoplasm (C) was measured (N:C ratio). The number of cells measured (n) is indicated for each condition.
Figure 12B:
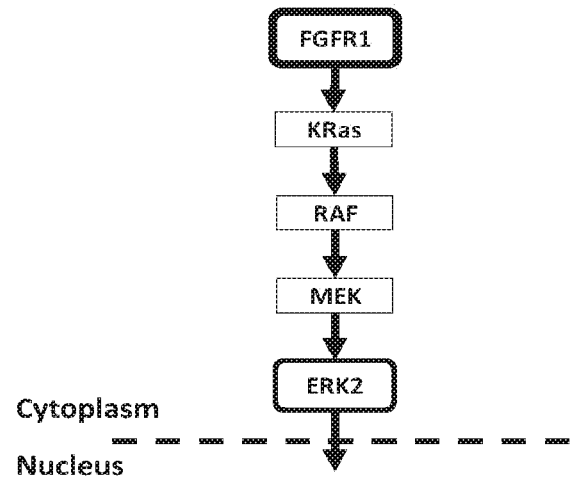
Figure 13A:
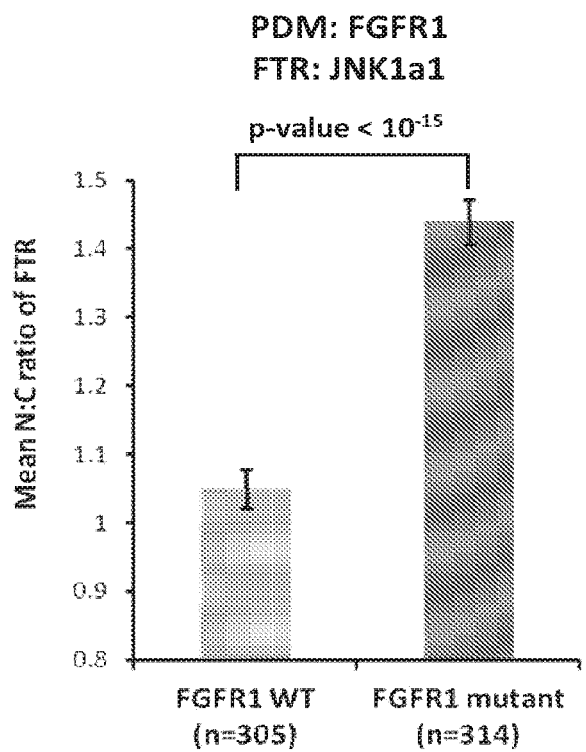
FIG. 13A—A bar graph showing results of a cell based assay in which the genes encoding FGFR1 in wild type (FGFR1 WT) or mutant form (FGFR1 mutant (A343V)) have been expressed in test cells, along with a reporter protein (FTR), and the amount of the FTR (JNKI a1-GFP) in the cytoplasm and in the nucleus was quantified, based on fluorescence microscope images of the cells (fixed 30 hours after transfection). The ratio between the intensity of the FTR (JNK1a1) in the nucleus (N) and cytoplasm (C) was measured (N:C ratio). The number of cells measured (n) is indicated for each condition.
Figure 13B:
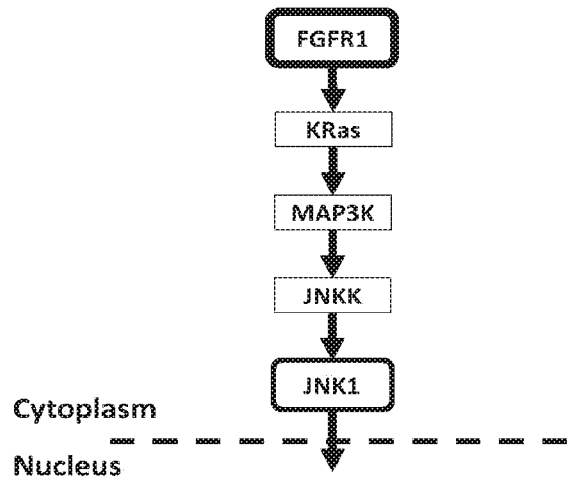
Figure 14A:
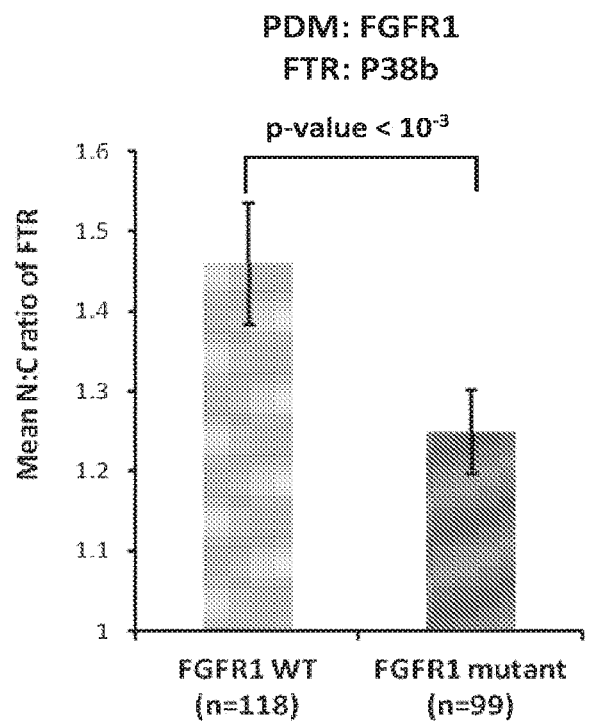
FIG. 14A—A bar graph showing results of a cell based assay in which the genes encoding FGFR1 in wild type (FGFR1 WT) or mutant form (FGFR1 mutant (A343V)) have been expressed in test cells, along with a reporter protein (FTR), and the amount of the FTR (P38b-GFP) in the cytoplasm and in the nucleus was quantified, based on fluorescence microscope images of the cells (fixed 30 hours after transfection). The ratio between the intensity of the FTR (P38b) in the nucleus (N) and cytoplasm (C) was measured (N:C ratio). The number of cells measured (n) is indicated for each condition.
Figure 14B:
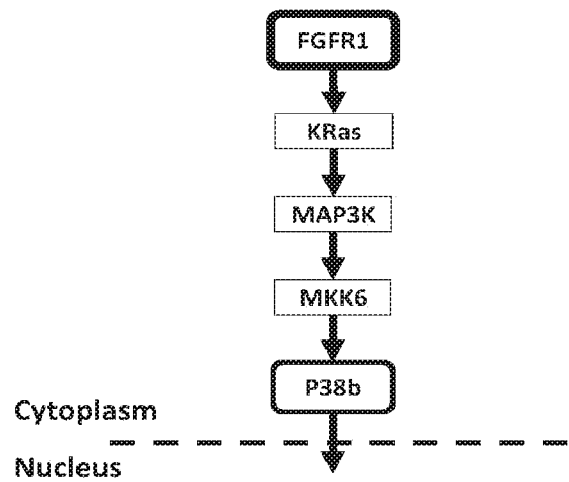
Figure 15A:
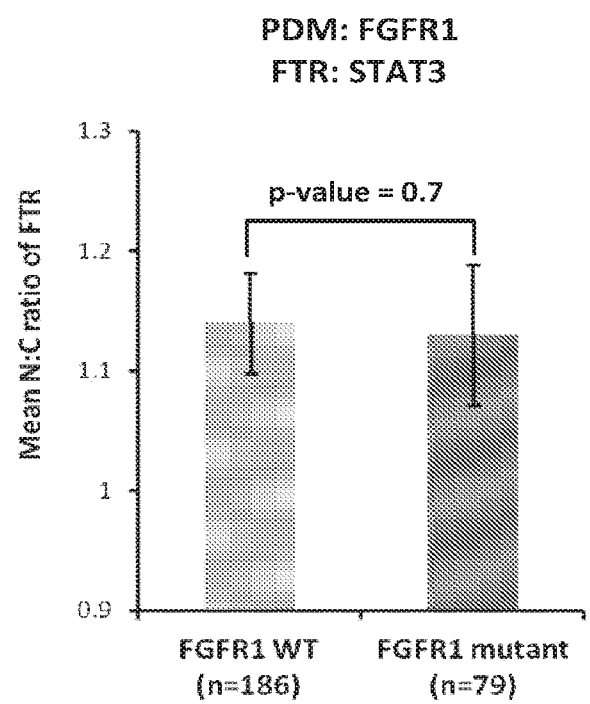
FIG. 15A—A bar graph showing results of a cell based assay in which the genes encoding FGFR1 in wild type (FGFR1 WT) or mutant form (FGFR1 mutant (A343V)) have been expressed in test cells, along with a reporter protein (FIR), and the amount of the FTR (STAT3-GFP) in the cytoplasm and in the nucleus was quantified, based on fluorescence microscope images of the cells (fixed 30 hours after transfection). The ratio between the intensity of the FTR (STAT3) in the nucleus (N) and cytoplasm (C) was measured (N:C ratio). The number of cells measured (n) is indicated for each condition.
Figure 15B:
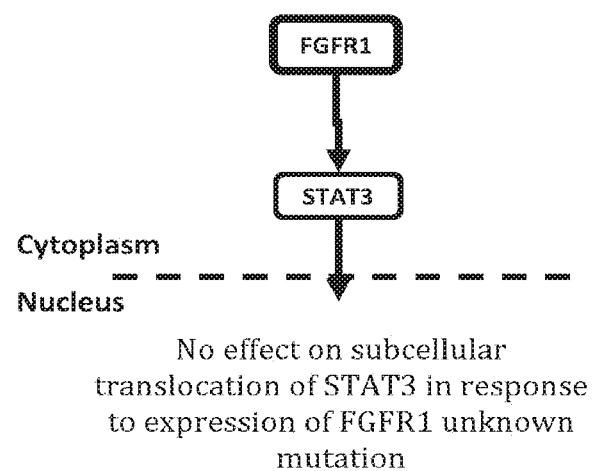
Figure 16A:
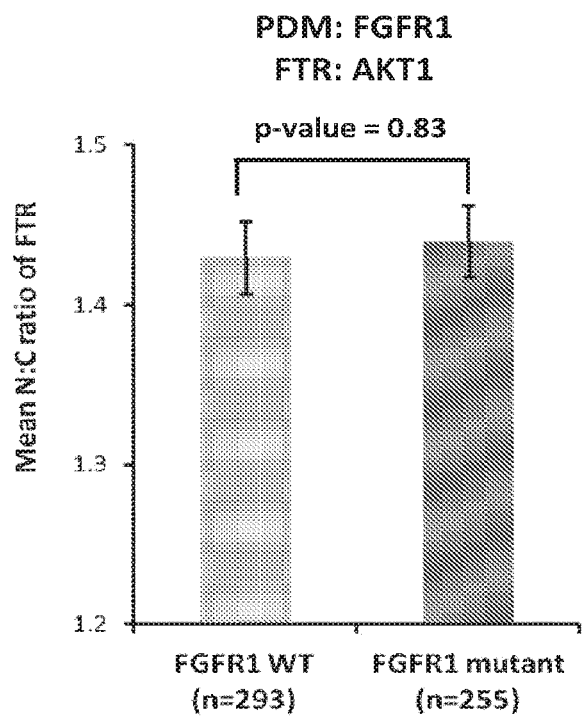
FIG. 16A—A bar graph showing results of a cell based assay in which the genes encoding FGFR1 in wild type (FGFR1 WT) or mutant form (FGFR1 mutant (A343V)) have been expressed in test cells, along with a reporter protein (FTR), and the amount of the FTR (AKT1-GFP) in the cytoplasm and in the nucleus was quantified, based on fluorescence microscope images of the cells (fixed 30 hours after transfection). The ratio between the intensity of the FTR (AKT) in the nucleus (N) and cytoplasm (C) was measured (N:C ratio). The number of cells measured (n) is indicated for each condition.
Figure 16B:
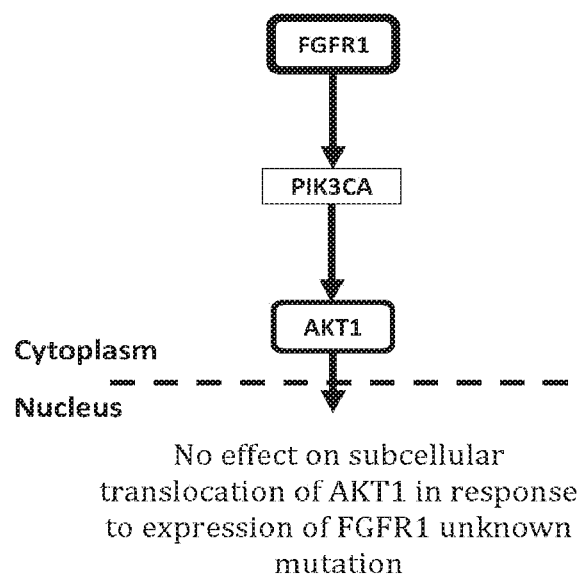

Example 5: Subcellular Translocation Assay of the ERK1/2, JNK and P38 Pathways can Discriminate Between the WT and Mutant FGFR1 and Identify FGFR1 Driver Mutations HeLa assay cells were transfected (as detailed above), with the indicated WT and mutated PDM (FGFR1-WT and mutated FGFR1 harboring a functionally unknown mutation (A343V), resides in the extracellular region, in an Ig-like C2-type 3 domain), along with a corresponding FTR. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 12A-16A. In FIG. 12A, the FTR is ERK2, in FIG. 13A, the FTR is JNK1alpha1, In FIG. 14A, the FTR is P38b, in FIG. 15A, the FTR is STAT3 and in FIG. 16A, the FTR is AKT1. FIGS. 12B-16B schematically show the oncogenic map of the signaling pathway affected by the PDM (FGFR1) as determined by the localization of the respective FTR. Altogether, the results show that the tested FGFR1 harboring a A343V mutation affects ERK1/2, JNK and p38 signaling pathways, but has no effect on the STAT pathway (FIGS. 15A-B) or the AKT pathway (FIGS. 16A-B).

Figure 17A:
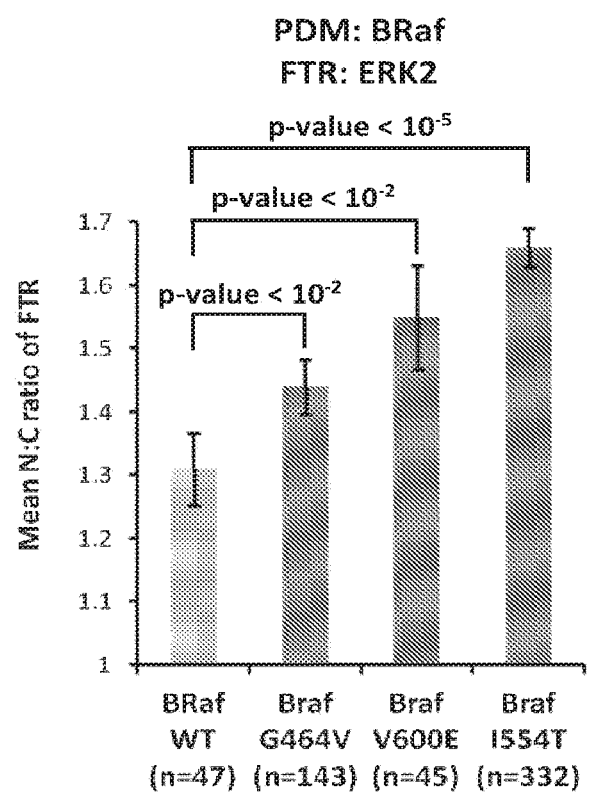
FIG. 17A—A bar graph showing results of a cell based assay in which the genes encoding BRAF in wild type (BRAF WT) or mutant forms (BRAF mutants G464V or V600E or 1554T) have been expressed in test cells, along with a reporter protein (FTR), and the amount of the FTR (ERK2-GFP) in the cytoplasm and in the nucleus was quantified, based on fluorescence microscope images of the cells (fixed 30 hours after transfection). The ratio between the intensity of the FTR (ERK2) in the nucleus (N) and cytoplasm (C) was measured (N:C ratio). The number of cells measured (n) is indicated for each condition.
Figure 17B:
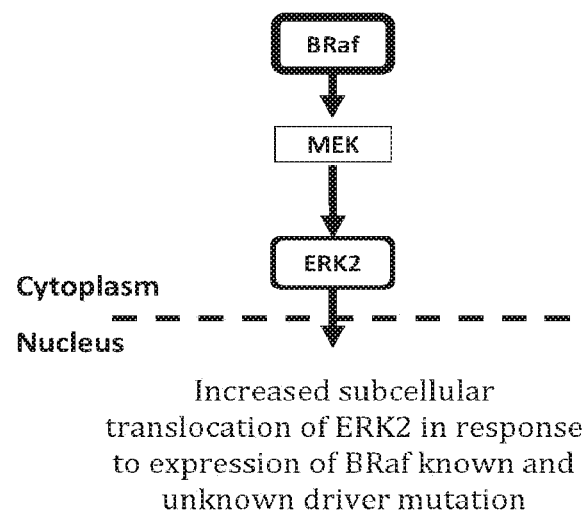
Figure 18A:
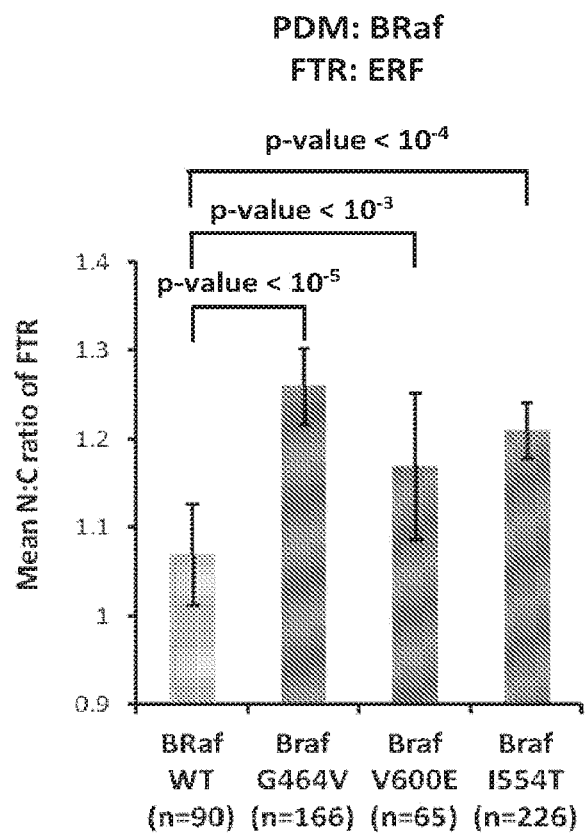
FIG. 18A—A bar graph showing results of a cell based assay in which the genes encoding BRAF in wild type (BRAF WT) or mutant forms (BRAF mutants G464V or V600E or 1554T) have been expressed in test cells, along with a reporter protein (FTR), and the amount of the FTR (ERF-GFP) in the cytoplasm and in the nucleus was quantified, based on fluorescence microscope images of the cells (fixed 30 hours after transfection). The ratio between the intensity of the FTR (ERF) in the nucleus (N) and cytoplasm (C) was measured (n) is indicated for each condition.
Figure 18B:
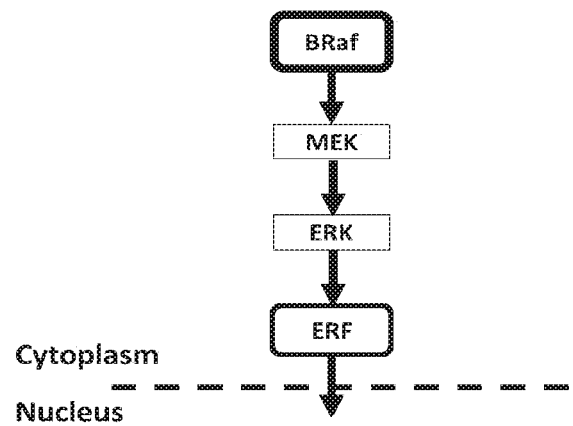

Example 6: Subcellular Translocation Assay of the ERK1/2 Pathway can Discriminate Between the WT and Mutant BRAF and Identify BRAF Driver Mutations HeLa assay cells were transfected (as detailed above), with a WT PDM (BRAF-WT) or the indicated mutated PDMs (mutated BRaf, harboring one of the following mutations: a known driver mutations (G464V), a known driver mutation (V600E) or a functionally unknown mutation (I554T), which resides in the kinase domain of BRAF), along with a corresponding FTR. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 17A-18A. In FIG. 17A, the FTR is ERK2 and in FIG. 18A, the FTR is ERF. FIGS. 17B-18B schematically show the oncogenic map of the signaling pathway affected by the PDM (BRAF) as determined by the localization of the respective FTR. Altogether, the results show that the two functionally known mutations (G464V and V600E) indeed activate the signaling pathway (as determined by both FTRs tested). The results further show that the also the functionally unknown mutation (I544T) also actives the tested signaling pathway, indicating that this is a driver mutation. Moreover, when using ERK2 as the FIR (FIG. 17A), the activation levels by the mutated BRAF harboring the functionally unknown I544T mutation, are as high as those observed for the BRAF harboring the known V600E mutation, which has been previously reported to be more active than the G464V mutation.

Thus, by using the methods disclosed herein, a BRAF mutant (I5441), not previously known to be active is identified as a functionally active mutant, capable of inducing aberrant signal 10 transduction pathway.

Figure 19A:
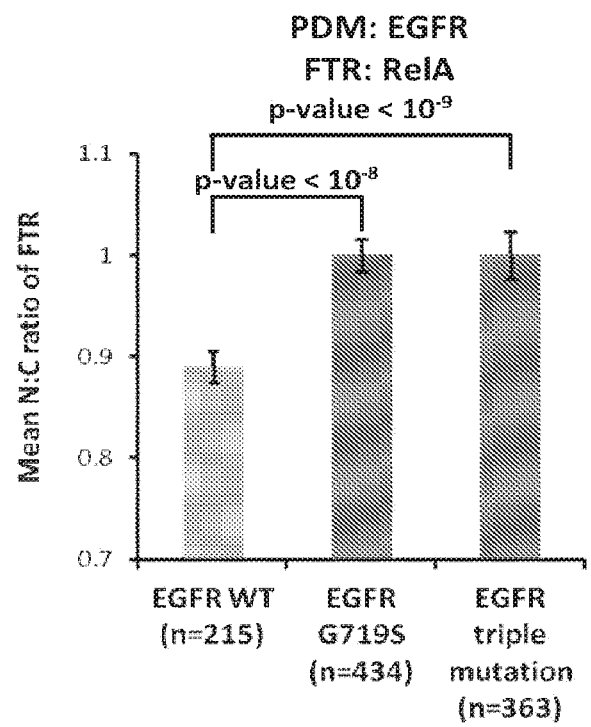
FIG. 19A—A bar graph showing the results of a cell based assay in which the genes encoding for EGFR in wild type form (EGFR WT), single mutant form (EGFR G719S) or triple mutant form (EGFR triple mutant, G719A, T790M and L861Q) have been expressed in test cells, along with a reporter protein (FTR), and the amount of the FTR (RelA-GFP) in the cytoplasm and in the nucleus was quantified based on fluorescence microscope images of the cells (fixed 30 hours after transfection). The ratio between the intensity of the FTR (RelA) in the nucleus (N) and cytoplasm (C) was measured (N:C ratio). The number of cells measured (n) is indicated for each condition.
Figure 19B:
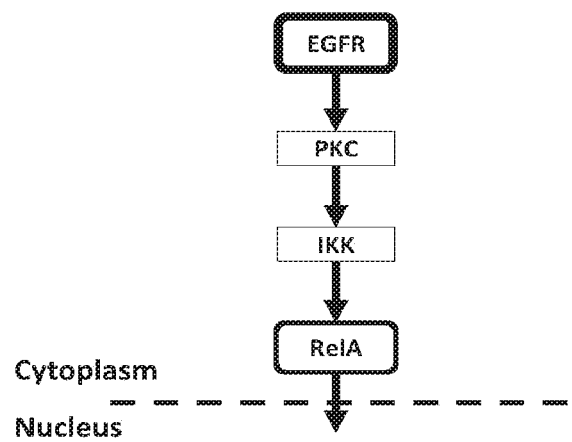
Figure 20A:
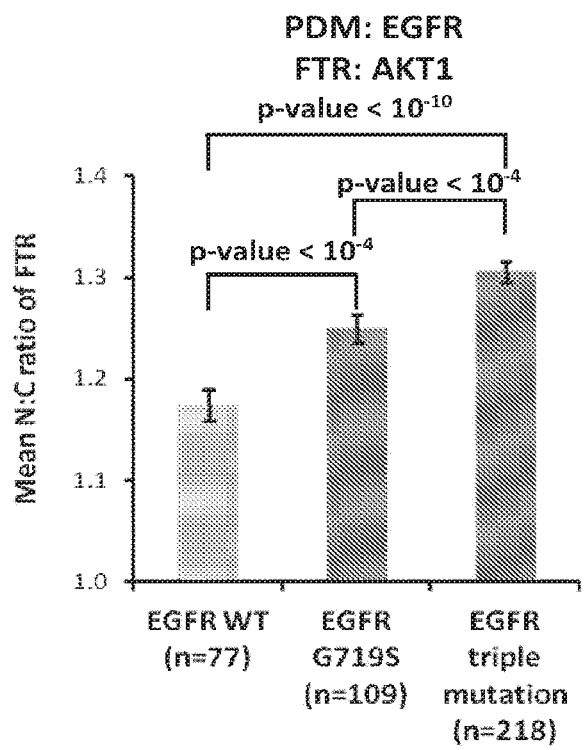
FIG. 20A—A bar graph showing the results of a cell based assay in which the genes encoding for EGFR in wild type form (EGFR WT), single mutant form (EGFR G719S) or triple mutant form (EGFR triple mutant, G719A, T790M and L861Q) have been expressed in test cells, along with a reporter protein (FTR), and the amount of the FTR (AKT1-GFP) in the cytoplasm and in the nucleus was quantified based on fluorescence microscope images of the cells (fixed 30 hours after transfection). The ratio between the intensity of the FTR (AKT1) in the nucleus (N) and cytoplasm (C) was measured (N:C ratio). The number of cells measured (n) is indicated for each condition.
Figure 20B:
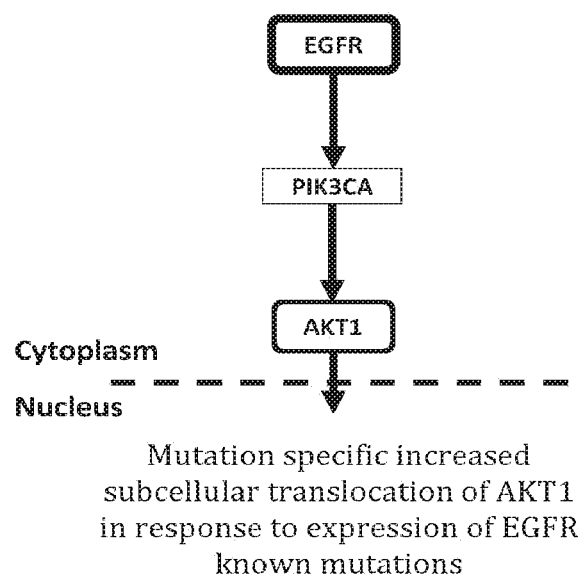
Figure 21A:
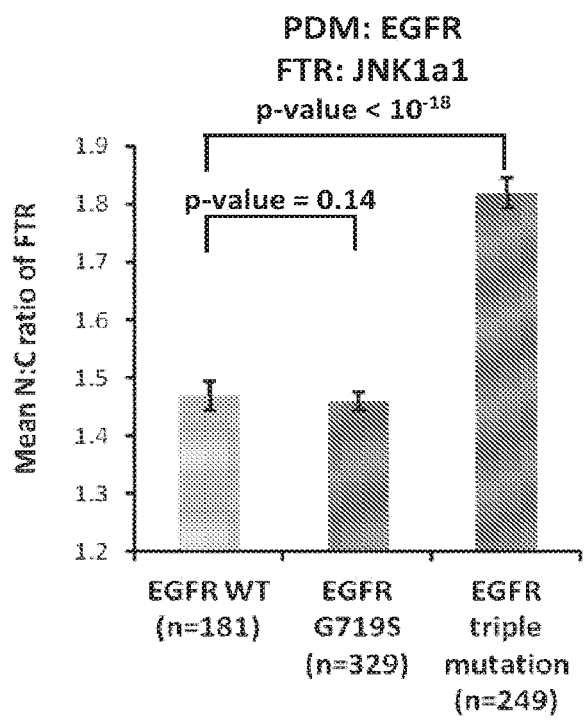
FIG. 21A—A bar graph showing the results of a cell based assay in which the genes encoding for EGFR in wild type form (EGFR WT), single mutant form (EGFR G719S) or triple mutant form (EGFR triple mutant, G719A, T790M and L861Q) have been expressed in test cells, along with a reporter protein (FTR), and the amount of the FTR (JNK1A1-GFP) in the cytoplasm and in the nucleus was quantified based on fluorescence microscope images of the cells (fixed 30 hours after transfection). The ratio between the intensity of the FTR (JNK1A1) in the nucleus (N) and cytoplasm (C) was measured (N:C ratio). The number of cells measured (n) is indicated for each condition.
Figure 21B:
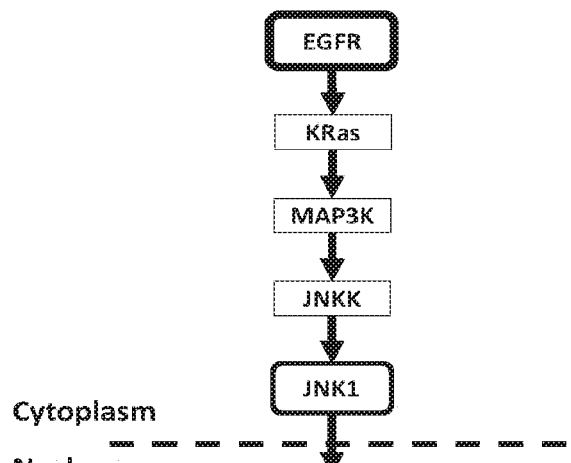
Figure 22A:
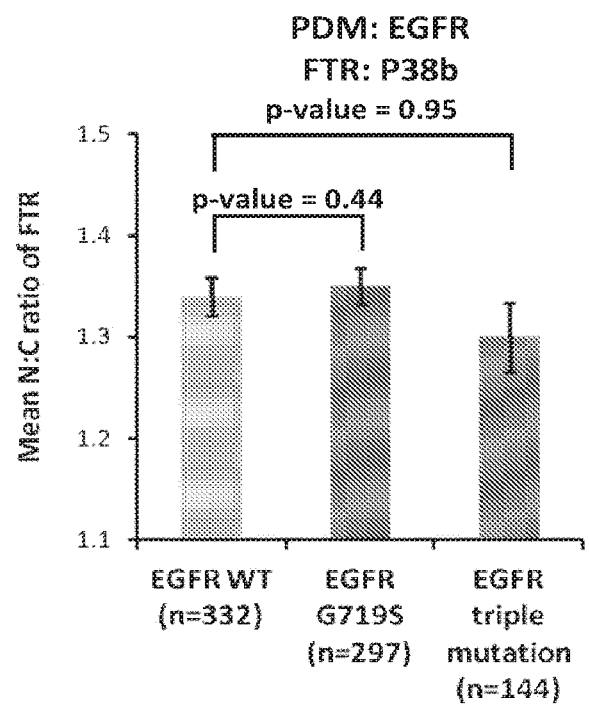
FIG. 22A—A bar graph showing the results of a cell based assay in which the genes encoding for EGFR in wild type form (EGFR WT), single mutant form (EGFR G719S) or triple mutant form (EGFR triple mutant, G719A, T790M and L861Q) have been expressed in test cells, along with a reporter protein (FTR), and the amount of the FTR (P38b-GFP) in the cytoplasm and in the nucleus was quantified based on fluorescence microscope images of the cells (fixed 30 hours after transfection). The ratio between the intensity of the FTR (P38b) in the nucleus (N) and cytoplasm (C) was measured (N:C ratio). The number of cells measured (n) is indicated for each condition.
Figure 22B:
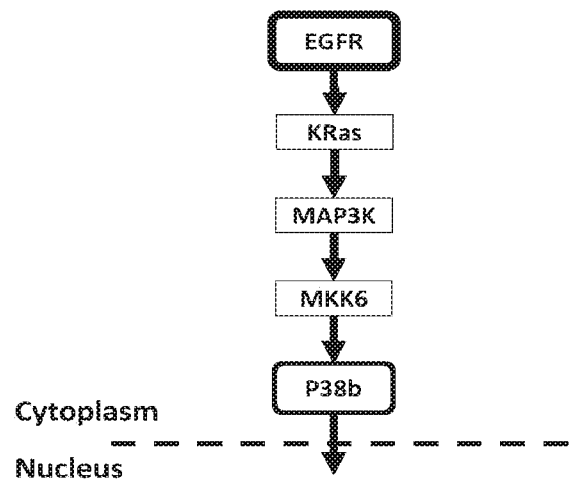
Figure 23A:
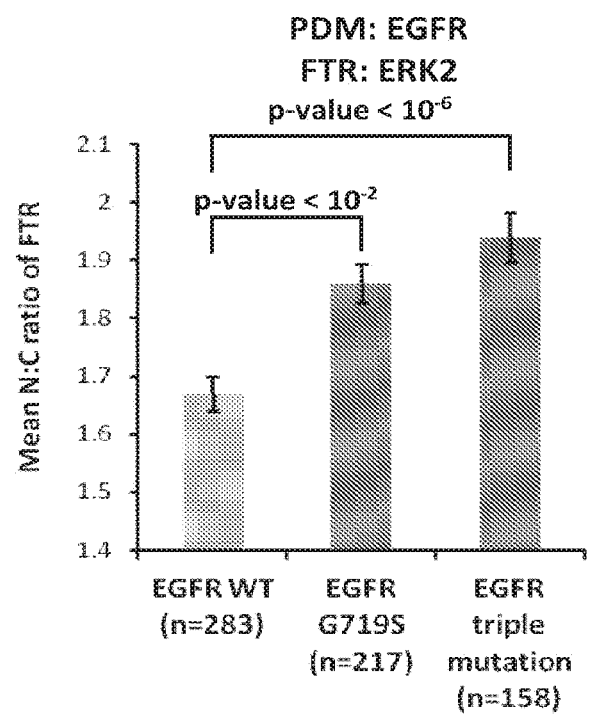
FIG. 23A—A bar graph showing the results of a cell based assay in which the genes encoding for EGFR in wild type form (EGFR WT), single mutant form (EGFR G719S) or triple mutant form (EGFR triple mutant, G719A, T790M and L861Q) have been expressed in test cells, along with a reporter protein (FTR), and the amount of the FTR (ERK2-GFP) in the cytoplasm and in the nucleus was quantified based on fluorescence microscope images of the cells (fixed 30 hours after transfection). The ratio between the intensity of the FTR (ERK2) in the nucleus (N) and cytoplasm (C) was measured (N:C ratio). The number of cells measured (n) is indicated for each condition.
Figure 23B:
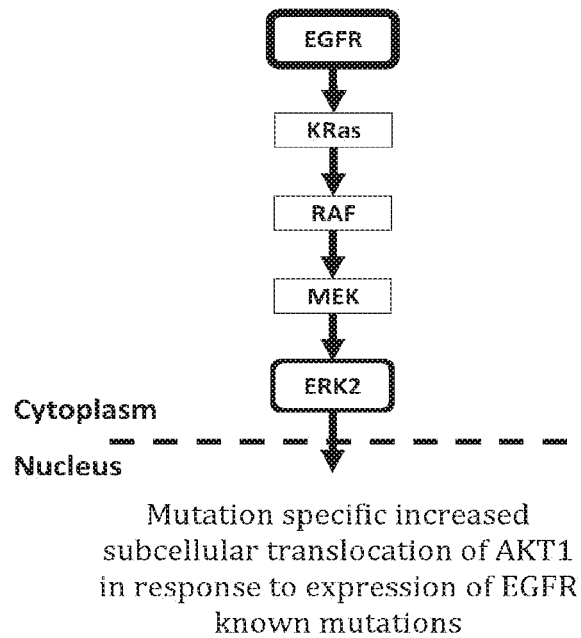

Example 7: Subcellular Translocation Assay of the NFkB, AKT and JNK Pathways can Discriminate Between the WT and Mutant EGFR and Grade EGFR Mutation Severity HeLa assay cells were transfected (as detailed above), with a WT PDM (EGFR-WT) or the indicated mutated PDMs (mutated EGFR, harboring one of the following mutations: a known driver mutations (G719S) or a mutant which includes three known driver mutations-G719A, T790M (known to confer resistance to small molecule EGFR inhibitors) and L861Q, (triple mutation)), along with a corresponding FTR. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 19A-23A. In FIG. 19A, the FTR is RelA, in FIG. 20A, the FTR is AKT1, in FIG. 21A, the FTR is Jnk1alpha1, in FIG. 22A, the FTR is P38beta and in FIG. 23A, the FTR is ERK2. FIGS. 19B-23B schematically show the oncogenic map of the signaling pathway affected by the PDM (EGFR) as determined by the localization of the respective FTR. Altogether, the results show that the tested EGFR mutants (G719S and the triple mutation) affects NFkB signaling pathway (FIGS. 19A-B), but has no effect on the P38 pathway (FIGS. 22A-B). Moreover, when using AKT1 as the FTR (FIG. 20A) or ERK2 as the FTR (FIG. 23A), both mutants activated this pathway, but the triple mutation (in a statistically significant way) to a larger manner than the G179S mutation. Likewise, when using JNK1alpha1 as the FTR (FIG. 21A), the activation levels by the G719S mutant was similar to the WT while the triple mutation caused activation of this pathway.

Thus, by using the methods disclosed herein, an EGFR triple mutation (G719A, T790M and L861Q) with inherent resistance to small molecule inhibitors, was shown to induce an enhanced signaling pathway activation pattern compared to a single driver mutation (G719S).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of identifying mutations causing aberrant signal transduction pathways in a sample from a cancer patient, comprising:
   a) providing assay cells that co-express: (i) a test expression construct comprising a mutated test gene encoding a protein comprising a mutation present in the patient or a control expression construct comprising the corresponding wild-type gene, and (ii) an expression vector encoding a Fluorescence Translocation Reporter (FTR) comprising a signaling protein linked to a fluorescent reporter protein, the signaling protein is downstream in a signaling pathway involving the protein expressed by the test and control expression constructs and changes its subcellular localization when the pathway is activated;
   b) incubating the assay cells for a sufficient period of time to allow expression of the mutated test gene or wild type gene and the FTR; and
   c) determining the subcellular localization of the FTR in the cells;
wherein the presence of the FTR in different subcellular locations in the test and control assays indicates that the gene mutation causes aberrant translocation of the signaling protein of the FTR.

2. The method of claim 1, wherein the subcellular localization is selected from: cytosol, nucleus, nucleolus, plasma membrane, endoplasmic reticulum (ER), mitochondria, Golgi apparatus, lysosomes, peroxisomes, endosomal compartments, and cytoskeleton.

3. The method of claim 1, wherein the signaling protein is selected from a tumor suppressor, a cytoskeleton protein, a growth factor receptor, a G-protein coupled receptor, a cell adhesion protein, a protein kinase, a transcription factor, an adaptor protein and an exchange factor.

4. The method of claim 1, wherein the fluorescent reporter protein is selected from: Green Fluorescent Protein (GFP), mCherry, mApple, DsRed, Red Fluorescent Protein (RFP), Blue Fluorescent Protein (BFP), EGFP, CFP, YFP, AmCyan1, ZsGreen1, ZsYellow1, DsRed2, AsRed2, and HcRed1.

5. The method of claim 1, wherein the assay cells are selected from HeLa cells, HEK 293 cells, U2OS, PC12, NCI60, A549, EKVX, T47D, HT29 and a cell of a cancer patient.

6. The method of claim 1, wherein a mutation causing aberrant signal transduction pathways identified by the method is a patient specific driver mutation.

* * * * *